(12) United States Patent
Heller et al.

(10) Patent No.: US 11,027,243 B2
(45) Date of Patent: Jun. 8, 2021

(54) GRAFTED ISLANDS-IN-THE-SEA NONWOVEN FOR HIGH CAPACITY ION EXCHANGE BIOSEPARATION

(71) Applicant: North Carolina State University, Raleigh, NC (US)

(72) Inventors: Michael Leonard Heller, Raleigh, NC (US); Ruben G. Carbonell, Raleigh, NC (US); Behnam Pourdeyhimi, Cary, NC (US)

(73) Assignee: North Carolina State University, Raleigh, NC (US)

( * ) Notice: Subject to any disclaimer, the term of this patent is extended or adjusted under 35 U.S.C. 154(b) by 217 days.

(21) Appl. No.: 15/748,988

(22) PCT Filed: Jul. 28, 2016

(86) PCT No.: PCT/US2016/044505
§ 371 (c)(1),
(2) Date: Jan. 30, 2018

(87) PCT Pub. No.: WO2017/019874
PCT Pub. Date: Feb. 2, 2017

(65) Prior Publication Data
US 2019/0001281 A1 Jan. 3, 2019

Related U.S. Application Data

(60) Provisional application No. 62/198,862, filed on Jul. 30, 2015.

(51) Int. Cl.
*B01D 15/36* (2006.01)
*B01D 67/00* (2006.01)
(Continued)

(52) U.S. Cl.
CPC ........... *B01D 71/82* (2013.01); *B01D 15/362* (2013.01); *B01D 15/363* (2013.01);
(Continued)

(58) Field of Classification Search
CPC ...... B01D 71/78; B01D 71/72; B01D 67/003; B01D 2323/345
See application file for complete search history.

(56) References Cited

U.S. PATENT DOCUMENTS 3,338,992 A  8/1967  Kinney
3,341,394 A  9/1967  Kinney
(Continued)

FOREIGN PATENT DOCUMENTS

CN  101781645 A  7/2010
EP  0713933 A1  5/1996
(Continued)

OTHER PUBLICATIONS

English translation of Singaporean Search Report and Written Opinion dated May 27, 2019, in corresponding Singaporean Patent Application No. 11201800641R (10 pages).
(Continued)

*Primary Examiner* — Bradley R Spies
(74) *Attorney, Agent, or Firm* — Thomas | Horstemeyer, LLP

(57) ABSTRACT

The invention provides polymer-grafted and functionalized nonwoven membranes adapted for use in bioseparation processes, the membranes including a nonwoven web of polyester fibers having an average fiber diameter of less than about 1.5 microns, each of the plurality of polyester fibers having grafted thereon a plurality of polymer segments constructed of a methacrylate polymer, each polymer segment carrying a functional group adapted for binding to a target molecule. The invention also provides a method of
(Continued)

bioseparation comprising passing a solution comprising the target molecule, such as a protein, through the nonwoven membrane of the invention such that at least a portion of the target molecule in the solution binds to the nonwoven membrane. A method for preparing a polymer-grafted and functionalized nonwoven membrane adapted for use in bioseparation processes is also provided.

10 Claims, 14 Drawing Sheets

(51) Int. Cl.
| | | |
|---|---|---|
| B01D 69/02 | (2006.01) | |
| B01D 71/40 | (2006.01) | |
| B01D 71/48 | (2006.01) | |
| B01D 71/78 | (2006.01) | |
| B01D 71/82 | (2006.01) | |
| B01J 39/19 | (2017.01) | |
| B01D 69/10 | (2006.01) | |
| B01J 41/13 | (2017.01) | |
| C07K 1/18 | (2006.01) | |
| D01F 8/14 | (2006.01) | |
| D04H 1/435 | (2012.01) | |
| D04H 1/4382 | (2012.01) | |
| D04H 3/011 | (2012.01) | |
| D04H 3/016 | (2012.01) | |
| D06M 13/203 | (2006.01) | |
| D06M 14/10 | (2006.01) | |
| D06M 14/28 | (2006.01) | |
| D06M 15/273 | (2006.01) | |
| D06M 101/32 | (2006.01) | |

(52) U.S. Cl.
CPC ....... *B01D 67/003* (2013.01); *B01D 67/0093* (2013.01); *B01D 69/02* (2013.01); *B01D 69/10* (2013.01); *B01D 71/40* (2013.01); *B01D 71/48* (2013.01); *B01D 71/78* (2013.01); *B01J 39/19* (2017.01); *B01J 41/13* (2017.01); *C07K 1/18* (2013.01); *D01F 8/14* (2013.01); *D04H 1/435* (2013.01); *D04H 1/4382* (2013.01); *D04H 3/011* (2013.01); *D04H 3/016* (2013.01); *D06M 13/203* (2013.01); *D06M 14/10* (2013.01); *D06M 14/28* (2013.01); *D06M 15/273* (2013.01); *B01D 2323/345* (2013.01); *B01D 2323/385* (2013.01); *B01D 2325/42* (2013.01); *D06M 2101/32* (2013.01); *D10B 2331/04* (2013.01); *D10B 2505/04* (2013.01)

(56) References Cited

U.S. PATENT DOCUMENTS

| | | | |
|---|---|---|---|
| 3,450,614 A * | 6/1969 | Faessinger | C08F 283/00 521/50.5 |
| 3,502,763 A | 3/1970 | Hartmann | |
| 3,542,615 A | 11/1970 | Dobo et al. | |
| 3,645,870 A * | 2/1972 | Sagane et al. | C08F 259/04 522/120 |
| 3,692,618 A | 9/1972 | Dorschner et al. | |
| 3,802,817 A | 4/1974 | Matsuki et al. | |
| 4,340,563 A | 7/1982 | Appel et al. | |
| 4,612,228 A | 9/1986 | Kato et al. | |
| 7,510,848 B2 | 3/2009 | Hammond et al. | |
| 7,981,226 B2 | 7/2011 | Pourdeyhimi et al. | |
| 8,101,425 B1 | 1/2012 | Carbonell | |
| 9,033,159 B1 | 5/2015 | Husson et al. | |
| 2009/0133810 A1 | 5/2009 | Penalva | |
| 2011/0318986 A1 * | 12/2011 | Pourdeyhimi | D04H 1/541 442/363 |
| 2013/0158518 A1 * | 6/2013 | Li | A61M 25/0045 604/529 |
| 2015/0299906 A1 | 10/2015 | Masuda et al. | |

FOREIGN PATENT DOCUMENTS

| | | |
|---|---|---|
| JP | 1-282390 A | 11/1989 |
| JP | 8-199480 A | 8/1996 |
| JP | 0952032 A | 2/1997 |
| JP | 2009-091707 | 4/2009 |
| JP | 2009-167128 A | 7/2009 |
| JP | 2012-229353 A | 11/2012 |
| JP | 2014-213313 A | 11/2014 |
| RU | 2350376 C2 | 3/2009 |
| WO | 2012/068442 A1 | 5/2012 |
| WO | 2013/129213 A1 | 9/2013 |

OTHER PUBLICATIONS

Communication pursuant to Article 94(3) EPC dated Apr. 11, 2019, in corresponding European Patent Application No. 16 831 357.5 (5 pages).
European Search Report dated Mar. 8, 2019, in corresponding European Patent Application No. 16 831 357.5 (4 pages).
Singaporean Second Office Action dated Oct. 8, 2019, in corresponding Singaporean Patent Application No. 11201800641R (6 pages).
Indian First Examination Report dated Oct. 31, 2019, in corresponding Indian Patent Application No. 201847004654, with English translation (7 pages).
International Search Report and Written Opinion in corresponding International Application No. PCT/US2016/044505, dated Nov. 8, 2016, 12 pages.
Russian Office Action dated Nov. 28, 2019, in corresponding Russian Application No. 2018107076/05, with English translation (6 pages).
Indonesian Office Action dated Nov. 6, 2019, in corresponding Indonesian Application No. P00201801501, with machine English translation (6 pages).
Brazilian Office Action dated Jan. 27, 2020, in corresponding Brazilian Application No. BR112018001581-4, with machine English translation (7 pages).
Indonesian Office Action dated Feb. 27, 2020, in corresponding Indonesian Application No. P0020181501, with English translation (7 pages).
Chinese First Office Action dated Mar. 30, 2020, in corresponding Chinese Application No. 201680057893.0, with English translation (21 pages).
Russian Office Action and Search Report dated Apr. 2, 2020, in corresponding Russian Application No. 2018107076/05, with English translation (14 pages).
Japanese Office Action dated Jun. 11, 2020, in corresponding Japanese Application No. 2018-525515, with English translation (8 pages).

\* cited by examiner

GRAFTED ISLANDS-IN-THE-SEA NONWOVEN FOR HIGH CAPACITY ION EXCHANGE BIOSEPARATION

CROSS REFERENCE TO RELATED APPLICATIONS

This patent application is the national phase of PCT/US2016/044505 filed Jul. 28, 2016, which claims the benefit of U.S. Application No. 61/198,862 filed Jul. 30, 2015.

FIELD OF THE DISCLOSURE

The present invention relates to polymer-grafted and functionalized nonwoven membranes adapted for use in bioseparation processes, as well as methods of forming and using the same.

BACKGROUND OF THE INVENTION

Membrane chromatography offers several potential advantages over traditional packed bed chromatography as a platform for bioseparations. The interconnected pores of membranes permit high rates of volumetric throughput without substantial pressure drops when compared to packed beds. Chromatographic resins need to be packed, they are not normally disposable, and as a result they require validated cleaning and regeneration processes for their use. On the other hand, many membranes can be made from polymers using scalable production techniques, enabling their use as stackable, ready-to-use, disposable bioseparation filters. Nonwoven membranes are particularly attractive for these applications since they are highly engineered to exhibit controllable porosities, fiber diameters, and pore sizes with low cost materials using high-rate manufacturing technologies. Protein binding to membranes is largely limited to the surface area created by the pores that are available for both flow and adsorption. This eliminates all diffusional limitations to adsorption, but it also reduces the binding capacity of membranes compared to chromatographic resins. Commercial nonwovens have a fraction of the surface area of chromatographic resins, resulting in low binding capacities for most target protein capture applications. By tethering polymer brushes to the surface of the fibers in a nonwoven membrane, 3-dimensional binding domains can be created that can substantially increase the overall protein binding capacity. Polymer brush grafting has been known to increase protein adsorption capacity by several times that of monolayer coverage in traditional chromatography resins, hollow fiber membranes, cast membranes, and nonwoven membranes.

Polymer grafting can change drastically the surface properties of supports. It can help tune the polarity of a surface to reduce or increase biomolecule adsorption and it can be used to introduce functional groups for ligand or spacer arm attachment in the 3-dimensional micro-environment introduced on the supporting interface. In a previous study conducted by Liu et al., glycidyl methacrylate (GMA) monomer was successfully grafted to a commercially available polybutylene terephthalate (PBT) nonwoven fabric. See H. Liu, Y. Zheng, P. Gurgel, R. Carbonell, Affinity membrane development from PBT nonwoven by photo-induced graft polymerization, hydrophilization and ligand attachment, J. Membr. Sci. 428 (2013) 562-575. Uniform and conformal polyGMA grafts were achieved around individual PBT fibers using UV-induced free radical polymerization. The polyGMA was attached directly to the PBT surface via hydrogen abstraction to initiate GMA polymerization using benzophenone (BP) as the initiator.

PBT is advantageous to use as a starting material for polyGMA grafting because it does not require the separate surface UV pretreatment necessary for grafting many polyolefins commonly used in the production of nonwoven fabrics. PBT nonwoven materials are inherently hydrophobic in nature leading to a high degree of nonspecific protein adsorption, making the base material itself a poor platform for bioseparations. Direct hydrolysis of polyGMA grafts on PBT using acidic conditions makes the fiber surface completely hydrophilic and substantially decreases nonspecific hydrophobic protein adsorption. Each monomer unit of GMA contains an epoxy end group that can be used to covalently attach ligands via nucleophilic substitution with available amines, thiols, and hydroxyl groups. In the study by Liu et al., diethylene glycol covalently attached to the polyGMA brushes was also found to substantially eliminate protein adsorption by nonspecific hydrophobic interactions.

PolyGMA grafted nonwovens offer a convenient platform for the development of effective ion exchange membranes. Saito et al. successfully grafted polyGMA brushes to polypropylene fabrics and polyethylene hollow fibers. See K. Saito, T. Kaga, H. Yamagishi, S. Furasaki, T. Sugo, J. Okamoto, Phosphorylated hollow fibers synthesized by radiation grafting and crosslinking, J. Membr. Sci. 43 (1989) 131-141. These grafted materials were functionalized with phosphoric acid groups to develop strong cation exchange membranes to capture divalent metal cations.

In a study by Zheng et al., polyGMA was grafted to polypropylene nonwoven and functionalized with diethyl amine (DEA) to develop a weak anion exchanger. See Y. Zheng, H. Liu, P. Gurgel, R. Carbonell, Polypropylene nonwoven fabrics with conformal grafting of poly(glycidyl methacrylate) for bioseparations, J. Membr. Sci. 364 (2010) 362-371. This material achieved equilibrium binding capacities for bovine serum albumin (BSA) of 120 mg/g of membrane.

Liu et al. investigated the effects of various degrees of polyGMA grafting on nonwoven PBT for the capture of BSA by anion exchange. See H. Liu, Surface modified nonwoven membranes for bioseparations, Raleigh N.C. USA, North Carolina State Univ., PhD thesis, 2012. In that study, polyGMA grafts were converted to weak anion exchangers with DEA and challenged with BSA. It was determined that the overall protein binding capacity increased with the degree of grafting (% weight gain). The largest equilibrium binding capacity of 800 mg/g was observed at a 12% polyGMA weight gain. This investigation also showed that residence times of several hours to a full day were required to reach maximum binding, and that these binding times increased with increased grafting weight % gain. These long residence times preclude the use of these polyGMA grafted nonwoven PBT membranes for the development of high throughput, high capacity protein capture devices for downstream processing.

Accordingly, there remains a need for grafted nonwoven membranes capable of high throughput, high capacity protein capture.

SUMMARY OF THE INVENTION

In one embodiment of the present invention, polybutylene terephthalate (PBT) nonwovens having an average fiber diameter of less than about 1.5 microns can be readily grafted with glycidyl methacrylate (GMA) or similar methacrylate polymers via, for example, UV-induced radical polymerization, to create uniform and conformal polymer brush networks around each fiber that can be chemically modified to function as anion or cation exchangers. The rates of adsorption of proteins by ion exchange were measured in an islands-in-the-sea (I/S) PBT nonwoven with average fiber diameter of approximately 1 µm in accordance with the present invention and in a commercially available PBT nonwoven with average fiber diameter of approximately 3 µm. Both nonwovens were grafted successfully with polyGMA and showed similar ion exchange equilibrium protein binding capacities at similar weight % grafting. However, the grafted I/S nonwoven membrane of the invention exhibited a substantially higher amount of protein binding in early stages and was able to reach equilibrium in a fraction of the time required by the grafted commercial nonwoven with larger fiber diameters. Although not bound by a theory of operation, the faster rate of protein adsorption observed with the I/S PBT nonwoven of the invention is believed to be the result of the thinner polyGMA graft layer thicknesses around the fibers compared to those in the commercial PBT with the same weight % grafting.

According to one aspect, the invention provides a polymer-grafted and functionalized nonwoven membrane adapted for use in bioseparation processes, comprising a nonwoven web comprising a plurality of polyester fibers (e.g. polybutylene terephthalate fibers), having an average fiber diameter of less than about 1.5 microns (more typically about 1 micron or less), each of the plurality of polyester fibers having grafted thereon a plurality of polymer segments constructed of a methacrylate polymer (e.g., polyGMA), each polymer segment carrying a functional group adapted for binding to a target molecule. In certain embodiments, the methacrylate polymer is constructed from one or more monomers selected from the group consisting of glycidyl methacrylate, methacrylic acid, 2-(diethylamino) ethyl methacrylate, [2-(methacryloyloxy)ethyl]trimethylammonium chloride, 2-hydroxyethyl methacrylate, 2-acrylamido-2-methylpropane sulfonic acid, 2-(dimethylamino) ethyl methacrylate, butyl methacrylate, 3-chloro-2-hydroxypropyl methacrylate, 2-ethylhexyl methacrylate, and combinations thereof. The functional group can vary depending on the target molecule, but will typically be a group adapted for cation or anion exchange with the target molecule.

In certain embodiments, the nonwoven web comprises island fibers remaining after removal of sea component of islands-in-the-sea bicomponent fibers. The nonwoven web can have an exemplary specific BET surface area of at least about 1.5 $m^2/g$. Typically, the weight of the grafted polymer segments is about 2 to about 50% of the weight of the nonwoven web, most preferably between 5 and 25% weight gain.

In another aspect, a method of bioseparation is provided, which comprises passing a solution comprising the target molecule, such as a protein, through the nonwoven membrane of the invention such that at least a portion of the target molecule in the solution binds to the nonwoven membrane.

In yet another aspect, the invention provides a method for preparing a polymer-grafted and functionalized nonwoven membrane adapted for use in bioseparation processes, comprising: receiving a nonwoven web comprising a plurality of islands-in-the-sea fibers or a plurality of island fibers remaining after removal of the sea component of bicomponent islands-in-the-sea fibers; optionally, removing the sea component of the bicomponent islands-in-the-sea fibers to expose the island fibers thereof; grafting a methacrylate polymer onto the surface of the island fibers to form a plurality of polymer segments covalently attached thereto, thereby forming grafted island fibers, the grafting step comprising contacting the nonwoven web with a solution comprising an initiator and at least one methacrylate monomer and exposing the nonwoven web to ultraviolet light to initiate polymerization of the methacrylate monomer; and optionally, functionalizing the grafted island fibers to attach at least one functional group adapted for binding to a target molecule to each of the plurality of polymer segments of the grafted island fibers. The concentration of monomer in the grafting solution can vary, but is typically about 5 to about 50% v/v (most preferably 15 to 25% v/v) and the initiator, such as benzophenone, is typically present in a molar ratio of initiator to monomer of about 1:100 to about 1:5 (e.g., 1:20). The ultraviolet light source can have wavelengths ranging from 200 nm to 500 nm (most preferably 365 nm) to initiate polymerization. The specific wavelength to initiate polymerization depends on the photoinitiator used, as well as, the monomer that is to be grafted to the surface of the PBT. Additionally, the ultraviolet light source can have intensities between 1 and 30 $mW/cm^2$ (most preferably 5 $mW/cm^2$), depending on the energy required for grafting and the desired rate at which grafting is to be performed to achieve the desired degrees of polymerization.

The invention includes, without limitation, the following embodiments:

Embodiment 1

A polymer-grafted and functionalized nonwoven membrane adapted for use in bioseparation processes, comprising a nonwoven web comprising a plurality of polyester fibers having an average fiber diameter of less than about 1.5 microns, each of the plurality of polyester fibers having grafted thereon a plurality of polymer segments constructed of a methacrylate polymer, each polymer segment carrying a functional group adapted for binding to a target molecule.

Embodiment 2

The membrane of any preceding or subsequent embodiment, wherein the methacrylate polymer is constructed from one or more monomers selected from the group consisting of glycidyl methacrylate, methacrylic acid, 2-(diethylamino) ethyl methacrylate, [2-(methacryloyloxy)ethyl]trimethylammonium chloride, 2-hydroxyethyl methacrylate, 2-acrylamido-2-methylpropane sulfonic acid, 2-(dimethylamino) ethyl methacrylate, butyl methacrylate, 3-chloro-2-hydroxypropyl methacrylate, 2-ethylhexyl methacrylate, and combinations thereof.

Embodiment 3

The membrane of any preceding or subsequent embodiment, wherein the polyester fibers are constructed of polybutylene terephthalate.

Embodiment 4

The membrane of any preceding or subsequent embodiment, wherein the average fiber diameter is about 1 micron or less.

Embodiment 5

The membrane of any preceding or subsequent embodiment, wherein the functional group is adapted for cation or anion exchange with the target molecule.

Embodiment 6

The membrane of any preceding or subsequent embodiment, wherein the nonwoven web comprises island fibers remaining after removal of the sea component of islands-in-the-sea bicomponent fibers.

Embodiment 7

The membrane of any preceding or subsequent embodiment, wherein the nonwoven web has a specific BET surface area of at least about 1.5 $m^2/g$.

Embodiment 8

The membrane of any preceding or subsequent embodiment, wherein the weight of the grafted polymer segments is about 2 to about 50% of the weight of the nonwoven web.

Embodiment 9

A method of bioseparation comprising passing a solution comprising the target molecule through the nonwoven membrane of any preceding or subsequent embodiment such that at least a portion of the target molecule in the solution binds to the nonwoven membrane.

Embodiment 10

The method of any preceding or subsequent embodiment, wherein the target molecule is a protein.

Embodiment 11

A method for preparing a polymer-grafted and functionalized nonwoven membrane adapted for use in bioseparation processes, comprising: i) receiving a nonwoven web comprising a plurality of islands-in-the-sea fibers or a plurality of island fibers remaining after removal of the sea component of bicomponent islands-in-the-sea fibers; ii) optionally, removing the sea component of the bicomponent islands-in-the-sea fibers to expose the island fibers thereof; iii) grafting a methacrylate polymer onto the surface of the island fibers to form a plurality of polymer segments covalently attached thereto, thereby forming grafted island fibers, the grafting step comprising contacting the nonwoven web with a solution comprising an initiator and at least one methacrylate monomer and exposing the nonwoven web to ultraviolet light or heat to initiate polymerization of the methacrylate monomer; and iv) optionally, functionalizing the grafted island fibers to attach at least one functional group adapted for binding to a target molecule to each of the plurality of polymer segments of the grafted island fibers.

Embodiment 12

The method of any preceding or subsequent embodiment, wherein the island fibers are constructed of polybutylene terephthalate and the methacrylate polymer is polyGMA.

Embodiment 13

The method of any preceding or subsequent embodiment, wherein the concentration of monomer in the solution is about 5 to about 50% v/v and the initiator is present in a molar ratio of initiator to monomer of about 1:100 to about 1:5.

Embodiment 14

The method of any preceding or subsequent embodiment, wherein the initiator is benzophenone.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise. Other aspects and advantages of the present invention will become apparent from the following.

BRIEF DESCRIPTION OF THE DRAWINGS

In order to provide an understanding of embodiments of the invention, reference is made to the appended drawings, which are not necessarily drawn to scale. The drawings are exemplary only, and should not be construed as limiting the invention.

DETAILED DESCRIPTION OF THE INVENTION

Figure 1:
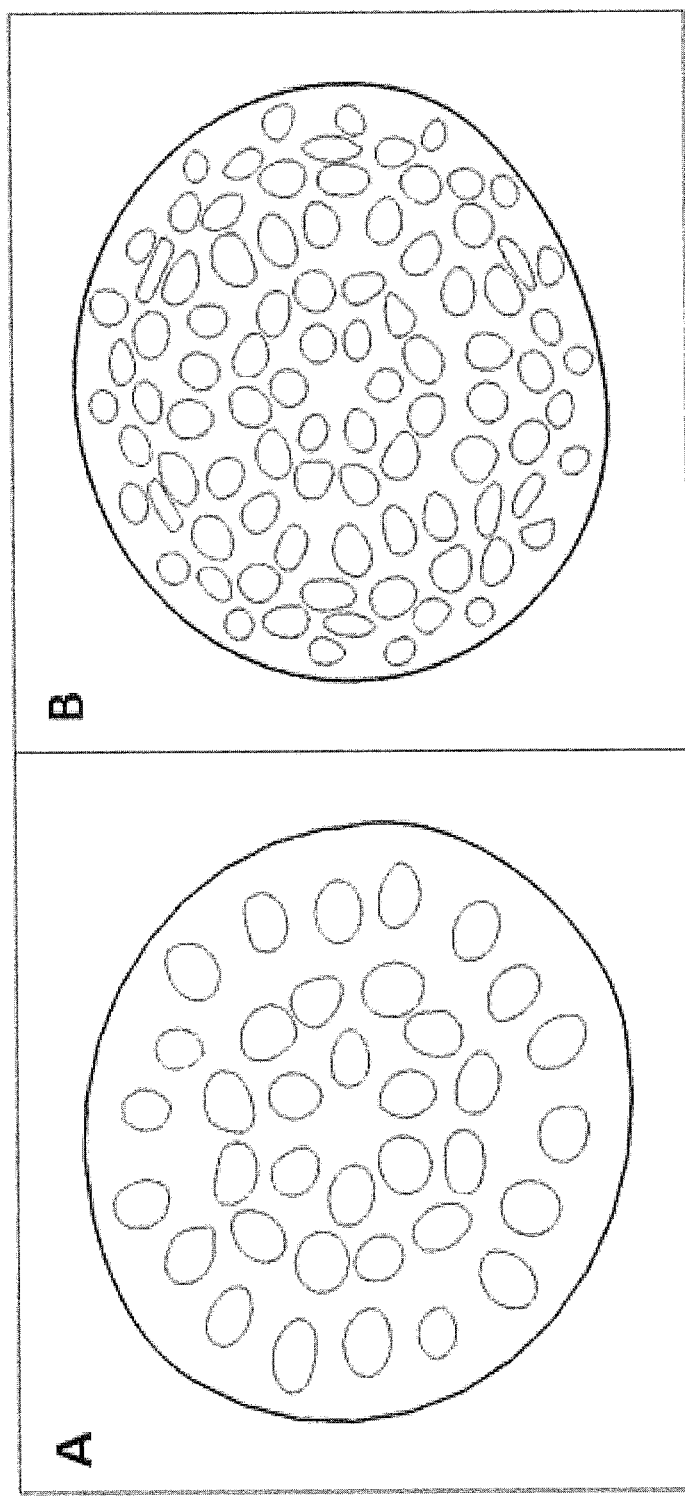
FIGS. 1A and 1B are cross-sectional views of (A) an I/S fiber with 36 islands and (B) an I/S fiber with 108 islands.

The present inventions now will be described more fully hereinafter with reference to the accompanying drawings. The inventions may be embodied in many different forms and should not be construed as limited to the embodiments set forth herein; rather, these embodiments are provided so that this disclosure will satisfy applicable legal requirements. Like numbers refer to like elements throughout. As used in this specification and the claims, the singular forms "a," "an," and "the" include plural referents unless the context clearly dictates otherwise.

The present invention utilizes a nonwoven web as a substrate for building a functionalized membrane capable of use for bioseparations, such as separation of proteins from certain solutions using ion exchange or affinity chromatography. The nonwoven web used in the present invention has an average fiber diameter in or close to the nanofiber range. A solution to the potential commercial production of nanofiber nonwovens is the utilization of bicomponent fibers in the spunbonding process for production of nonwoven mats. See, e.g., N. Fedorova, B. Pourdeyhimi, High strength nylon micro- and nanofiber based nonwovens via spunbonding, J. Appl. Polym. Sci. 104 (2007) 3434-3442. In this production scheme, two polymers can be coextruded from the same spinneret where they combine to become a cohesive fiber. The fibers can also be extruded in a segmented pie or core in sheath configuration. These fibers can then be fractured to release many fibers of much smaller diameter, or one of the polymers can be selectively dissolved, leaving a much smaller set of fibers in the nonwoven matrix. See, e.g., A. Durany, N. Anantharamaiah, B. Pourdeyhimi, High surface area nonwovens via fibrillating spunbonded nonwovens comprising Islands-in-the-Sea bicomponent filaments: structure-process-property relationships, J. Mater. Sci. 44 (2009) 4926-5934.

As used herein, the term "fiber" is defined as a basic element of textiles which has a high aspect ratio of, for example, at least about 100 times. In addition, "filaments/continuous filaments" are continuous fibers of extremely long lengths that possess a very high aspect ratio. The term "multicomponent fibers" refers to fibers that comprise two or more polymers that are different by physical or chemical nature including bicomponent fibers. The term "nonwoven" as used herein in reference to fibrous materials, webs, mats, batts, or sheets refers to fibrous structures in which fibers are aligned in an undefined or random orientation. The fibers according to the present invention can vary, and include fibers having any type of cross-section, including, but not limited to, circular, rectangular, square, oval, triangular, and multi-lobal. In certain embodiments, the fibers can have one or more void spaces, wherein the void spaces can have, for example, circular, rectangular, square, oval, triangular, or multi-lobal cross-sections.

The means of producing a nonwoven web can vary. In general, nonwoven webs are typically produced in three stages: web formation, bonding, and finishing treatments. Web formation can be accomplished by any means known in the art. For example, webs may be formed by a drylaid process, a spunlaid process, or a wetlaid process. In various embodiments of the present invention, the nonwoven web is made by a spunbonding process. Spunbonding can employ various types of fiber spinning process (e.g., wet, dry, melt, or emulsion). Melt spinning is most commonly used, wherein a polymer is melted to a liquid state and forced through small orifices into cool air, such that the polymer strands solidify according to the shape of the orifices. The fiber bundles thus produced are then drawn, i.e., mechanically stretched (e.g., by a factor of 3-5) to orient the fibers. A nonwoven web is then formed by depositing the drawn fibers onto a moving belt. General spunbonding processes are described, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al., which are all incorporated herein by reference. Spunbonding typically produces a larger diameter filament than meltblowing, for example. For example, in some embodiments, spunbonding produces fibers having an average diameter of about 20 microns or more.

Various methods are available for processing multicomponent fibers to obtain fibers having smaller diameters (e.g., less than about 1.5 microns, less than about 1.0 micron, or less than about 0.5 microns). Although these methods are commonly applied to spunbonded materials, which typically have larger diameters, it is noted that they can also be applied to meltblown materials as well as fibrous materials prepared by other means. For example, in some embodiments, splittable multicomponent fibers are produced (e.g., including but not limited to, segmented pie, ribbon, islands in the sea, or multilobal) and subsequently split or fibrillated to provide two or more fibers having smaller diameters. The means by which such fibers can be split can vary and can include various processes that impart mechanical energy to the fibers, such as hydroentangling. Exemplary methods for this process are described, for example, in U.S. Pat. No. 7,981,226 to Pourdeyhimi et al., which is incorporated herein by reference.

As noted above, in certain embodiments, multicomponent fibers are produced and subsequently treated (e.g., by contacting the fibers with a solvent) to remove one or more of the components. For example, in certain embodiments, an islands-in-the-sea fiber can be produced and treated to dissolve the sea component, leaving the islands as fibers with smaller diameters. Exemplary methods for this type of process are described, for example, in U.S. Pat. No. 4,612,228 to Kato et al., which is incorporated herein by reference.

The Islands-in-the-Sea (I/S) nonwoven technology is an extension of the core in sheath bicomponent filament process. This type of nonwoven has many permanent polymer cores within the fiber known as "islands" embedded in a sacrificial polymer sheath known as the "sea". The number of islands and ratio of islands to sea component are not particularly limited in the present invention, with an exemplary range of the number of islands including about 20 to about 400 islands (e.g., about 50 to about 200 islands). FIGS. 1A and 1B are cross-sectional view of two exemplary I/S structures, one with 36 islands and one with 108 islands. The ratio of "islands" to "sea" can range, for example, from about 25:75 (w:w) to about 75:25 (w:w). Polylactic acid (PLA) has a lower melting temperature compared to many polymers (e.g., nylon-6 and PBT) and can easily be decomposed with a hot caustic bath, making it a great candidate for a dissolvable "sea". I/S nonwovens are capable of achieving smaller fiber diameters and therefore, higher specific surface areas, compared to commercially available nonwovens made by meltblown or spunbond technologies while still conserving high productivity of fiber production and dimensional stability.

The fibrous webs thus produced can have varying basis weight. In some embodiments, the basis weight of the nonwoven web is about 200 g/m$^2$ or less, about 150 g/m$^2$ or less, about 100 g/m$^2$ or less, or about 50 g/m$^2$ or less. In certain embodiments, the nonwoven fabric has a basis weight of about 75 g/m$^2$ to about 125 g/m$^2$. The basis weight of the a fabric can be measured, for example, using test methods outlined in ASTM D 3776/D 3776M-09ae2 entitled "Standard Test Method for Mass Per Unit Area (Weight) of Fabric." This test reports a measure of mass per unit area and is measured and expressed as grams per square meter (g/m$^2$).

The nonwoven web can have an exemplary specific BET surface area of at least about 1.5 m$^2$/g, such as at least about 2.0 m$^2$/g or at least about 2.2 m$^2$/g. An exemplary BET surface area range is about 1.5 m$^2$/g to about 3.0 m$^2$/g.

The polymer of the nonwoven web can vary, but will typically comprise a thermoplastic polymer that is well-suited for grafting. Exemplary polymers include polyolefins (e.g., polyethylene or polypropylene), polyesters, and polyamides. Polyesters are particularly useful, including polybutylene terephthalate (PBT), polytrimethylene terephthalate (PTT), polyethylene terephthalate (PET), co-polyesters, and combinations thereof. PBT is particularly useful because the polymer structure of PBT has natural affinity for certain initiators used in grafting reactions, such as benzophenone. For this reason, a pretreatment step to introduce functional groups to the polymer in order to enhance affinity between the polymer and the initiator is not necessary when using PBT.

As noted above, the polymeric fibers of the nonwoven web are subjected to a grafting process through which polymeric brushes or segments are covalently attached to the fibers. This process typically entails contacting the nonwoven web with a solution comprising a monomer dissolved in a suitable solvent, along with a free radical polymerization initiator, such as a photoinitiator (e.g., benzophenone). The process typically also entails subjecting the nonwoven web to ultraviolet light with wavelengths between 200 and 500 nm (most preferably 365 nm) and with intensities between 1 and 30 mW/cm$^2$ (most preferably 5 mW/cm$^2$) to initiate the polymerization reaction. The concentration of monomer in the grafting solution can vary, but is typically about 5 to about 50% v/v (most preferably 15-25% (v/v)) and the initiator, such as benzophenone, is typically present in a molar ratio of initiator to monomer of about 1:100 to about 1:5 (e.g., 1:20). In certain embodiments, the polymerization reaction is allowed to proceed until the weight of the grafted polymer segments is about 2 to about 50% of the weight of the nonwoven web (most preferably 5-25% weight gain).

The polymer used for grafting can vary, but will typically be an acrylate or methacrylate polymer. The grafting polymer provides brush-like extensions to the fibers of the nonwoven web that can be functionalized to enhance affinity for certain target molecules. The selection of monomer for the graft polymer can vary, and will depend in part, on the desired binding properties needed for the final membrane structure. Certain monomers will inherently carry functional groups that can be used for affinity or ion exchange binding while other monomers will require further functionalization to add the necessary binding groups. Exemplary monomers and possible uses thereof include: glycidyl methacrylate (suitable for further functionalization), methacrylic acid (weak cation exchange membranes), 2-(diethylamino)ethyl methacrylate (weak anion exchange membranes), [2-(methacryloyloxy)ethyl]trimethyl-ammonium chloride (strong anion exchange membranes), 2-hydroxyethyl methacrylate (HEMA, protein resistant membranes), 2-acrylamido-2-methylpropane sulfonic acid (strong cation exchange membranes), 2-(dimethylamino)ethyl methacrylate (weak anion exchange membranes), butyl methacrylate (hydrophobic interaction membranes), 3-chloro-2-hydroxypropyl methacrylate (suitable for further functionalization), 2-ethylhexyl methacrylate (hydrophobic interaction membranes), and combinations thereof.

If necessary, the polymer segments or brushes can be functionalized such that each polymer segment carries a functional group adapted for binding to a target molecule. Exemplary binding that can occur between such functional groups and a target molecule, such as a protein, can include ionic bonds, hydrogen bonds, and van der Waals forces. Exemplary functional groups include amine groups (including primary, secondary, tertiary or quaternary amines), sulfonic acid groups, carboxylic acid groups, phosphate groups, and the like. The derivatizing reactions to attach such functional groups typically involve reacting an epoxy group or other reactive group on the polymer brush with a molecule containing the desired functional group.

As set forth more fully in the Experimental section, the inventors successfully grafted complete and conformal polyGMA brushes to 108 island I/S PBT nonwoven webs. The grafted nonwovens were successfully derivatized to be weak anion and strong cation exchangers for capture of BSA and hIgG, respectively. Equilibrium static protein binding capacities as high as 1000 mg/g for 18-20% polyGMA weight gain were achieved, indicating that polyGMA brushes were capable of increasing protein capture several times that of monolayer coverage. It was observed that the higher surface area 108 I/S PBT nonwoven with thinner polyGMA grafts was capable of reducing the significance of the diffusion limitation in the polyGMA/protein layer, resulting in shorter times to reach equilibrium compared to a commercial PBT nonwoven. Additionally, the 108 I/S nonwoven PBT demonstrated a higher amount of initial protein binding compared to the commercial PBT nonwoven, which is advantageous in applications requiring short residence times.

In certain embodiments, the polymer-grafted and functionalized nonwoven membranes of the invention can be characterized by very high protein binding capacities, such as a capacity of at least about 800 mg/g, at least about 850 mg/g, or at least about 900 mg/g of protein at a graft polymer weight gain of at least about 18% (e.g., a nonwoven comprising 18-20% by weight of graft polymer, based on the weight of the nonwoven web). Additionally, the nonwoven webs of the invention can be characterized as binding significant amounts of protein in short contact periods, such as protein binding of at least about 200 mg/g, at least about 250 mg/g, or at least about 300 mg/g in a contact period of no more than about one minute, at a graft polymer weight gain of at least about 18% (e.g., a nonwoven comprising 18-20% by weight of graft polymer, based on the weight of the nonwoven web).

EXPERIMENTAL

Islands-in-the-sea nonwoven PBT fabrics with a 108 island count were produced on the pilot facilities at the Nonwovens Institute (NWI, North Carolina State University, Raleigh, N.C.). The island count refers to the number of discrete PBT fibers that are liberated once the PLA "sea" has been removed. The US nonwoven was manufactured with a basis weight of 100 g/m² consisting of 50% PLA as the "sea" polymer and 50% PBT as the "island" polymer, the basis weight after "sea" removal is 50 g/m². Macopharma (Tourcoing, France) provided commercially available meltblown PBT nonwovens with a basis weight of 52 g/m². Glycidyl methacrylate (GMA) was purchased from Pflatz & Bauer (Waterbury, Conn.). Inhibitors in GMA were removed through a pre-packed inhibitor removal column to remove hydroquinone and monomethyl ether hydroquinone (Sigma Aldrich, St. Louis, Mo.). Benzophenone (BP) was purchased from Sigma Aldrich (St. Louis, Mo.). Sodium hydroxide, 1-butanol, tris base, hydrochloric acid, sodium chloride and sodium acetate trihydrate were purchased from Fisher Scientific (Fairlawn, N.J.). Tetrahydrofuran (THF), methanol, sulfuric acid, and acetic acid were purchased from BDH (West Chester, Pa.). Diethylamine (DEA) was purchased from Alfa Aesar (Ward Hill, Mass.). Phosphoric acid (85%) was purchased from Acros Organics (Fairlawn, N.J.). Solid phase extraction tubes were purchased from Supelco (Bellefonte, Pa.). Albumin from bovine serum (BSA) was purchased from Sigma Aldrich (St. Louis, Mo.). Human immunoglobulin G (hIgG) was purchased from Equitek-Bio Inc. (Kerrville, Tex.).

PLA Removal from I/S Nonwovens

The 50% PLA "sea" of the 108 I/S nonwovens had to be removed to liberate the PBT "islands" prior to grafting. PLA was decomposed using 10% w/w sodium hydroxide in DI water at 80-90° C. I/S nonwovens were submerged in caustic bath for 5 min with constant stirring until all of the PLA had been dissolved from the nonwovens. The PBT nonwovens were then washed extensively with DI water until a neutral pH was achieved. Samples were then allowed to air dry overnight. FIGS. 2A and 2B display a 108 I/S PBT nonwoven before and after the removal of PLA, respectively.

In FIG. 2A PLA is still present, encapsulating the PBT "islands", showing the initial larger fibers of about 15 μm in diameter prior to PLA removal. FIG. 2B shows the nonwoven post PLA removal to liberate 108 discreet PBT fibers that are approximately 1 μm in diameter. The PBT fibers released after PLA removal maintain the general direction of the original PLA fibers.

UV-Induced polyGMA Grafting onto PBT Nonwovens

The GMA grafting solution consisted of 20% v/v GMA monomer in 1-butanol as the solvent. The photoinitiator benzophenone (BP) was added to the grafting solution in a BP:GMA ratio of 1:20 (mol:mol). Commercially available PBT nonwovens and 108 I/S PBT nonwovens after PLA removal were cut to 75×50 mm size samples and weighed prior to grafting, samples were approximately 200 mg and 180 mg for commercial PBT and 108 I/S PBT respectively. Nonwovens were saturated with grafting solution by spraying 1.5-2.0 ml of grafting solution via syringe, and placed between two borosilicate glass slides (75×50 mm). A UV lamp (model EN-180L, Spectronics Corporation, Westbury, N.Y.) with a 365 nm wavelength and an intensity of 5 mW/cm² was used to induce free radical polymerization of the GMA onto the PBT surface. The distance between the lamp and the sample was 3 mm. Samples were irradiated at various exposure times to achieve different degrees of polyGMA grafting with different % weight gains. After polyGMA grafting, the samples were placed in a flask containing 100 ml of THF, the flask with the THF and samples was sonicated with an ultrasonic bath (Bransonic 3510R-MT, Branson Ultrasonics Corporation, Danbury, Conn.) for 30 min to remove any unreacted grafting solution or untethered polyGMA. Following the THF wash the samples were removed from the flask and placed in a flask containing 100 ml of methanol, the flask containing the samples and methanol was sonicated with an ultrasonic bath for 10 min to remove THF from the nonwovens. Following the methanol wash the samples were removed from the flask and allowed to dry in air overnight. The final weight of the nonwovens was measured and the degree of polyGMA grafting was determined using Eq. 1 in terms of a % weight gain due to grafting.

$$\text{Degree of } polyGMA \text{ grafting (\% weight gain)} = \frac{W_f - W_i}{W_i} \times 100\% \quad (1)$$

In Eq. 1, $W_i$ is the initial nonwoven weight prior to grafting and $W_f$ is the final nonwoven weight after polyGMA grafting. The % weight gain defined in Eq. 1 is abbreviated as % Wt. Gain in the figures presented in this paper.

Functionalization of polyGMA Grafted PBT Nonwovens

PolyGMA grafted PBT nonwovens were functionalized to produce weak anion exchangers by immersion in 50% v/v aqueous diethyl amine (DEA) solution, thus creating a tertiary amine on the polyGMA brushes. Grafted PBT nonwoven samples between 180 and 200 mg (75×50 mm) were immersed in 100 ml of the DEA solution. The reaction was kept at a constant 30° C. with agitation at 100 rpm using an incubation shaker (Certomat® RM, B. Braun Biotech International, Melsungen, Germany) contained in an incubation hood (Certomat® HK, B. Braun Biotech International, Melsungen, Germany). Following amination, samples were placed in a flask containing 100 ml of DI water, the flask was placed in an ultrasonic bath (Bransonic 3510R-MT, Branson Ultrasonics Corporation, Danbury, Conn.) for 5 min, to remove excess DEA. Following sonication, the DI water wash was replaced with fresh DI water and the process was repeated until a neutral pH of 7.0 was verified with pH testing paper, 10 washes ensured that all DEA had been removed from the nonwoven. Any unreacted epoxy groups were hydrolyzed by immersion of the sample in 100 ml of 100 mM sulfuric acid overnight. Following hydrolysis of the epoxy groups, samples were placed in a flask containing 100 ml of DI water, the flask was placed in an ultrasonic bath (Bransonic 3510R-MT, Branson Ultrasonics Corporation, Danbury, Conn.) for 5 min, to remove excess sulfuric acid. Following sonication, the DI water wash was replaced with fresh DI water and the process was repeated until a neutral pH of 7.0 was verified with pH testing paper, 10 washes ensured that all the sulfuric acid had been removed from the nonwoven. The samples were then air dried overnight.

PolyGMA grafted PBT nonwovens were functionalized to create strong cation exchangers by attaching phosphoric acid groups to the polyGMA brushes. Approximately 20 mg (25×15 mm) of grafted PBT nonwoven samples were immersed in 10 ml of 85% w/w phosphoric acid and incubated at 80° C. overnight (Isotemp 115, Fisher Scientific, Fairlawn, N.J.). Following functionalization the samples were placed in a flask containing 100 ml of DI water, the flask was placed in an ultrasonic bath (Bransonic 3510R-MT, Branson Ultrasonics Corporation, Danbury, Conn.) for 5 min, to remove excess phosphoric acid. Following sonication, the DI water wash was replaced with fresh DI water and the process was repeated until a neutral pH of 7.0 was verified with pH testing paper, 5 washes ensured that all phosphoric acid had been removed from the nonwoven. Any unreacted epoxy groups were hydrolyzed by immersion of the sample in 10 ml of 100 mM sulfuric acid overnight. Following hydrolysis of the epoxy groups, samples were placed in a flask containing 100 ml of DI water, the flask was placed in an ultrasonic bath (Bransonic 3510R-MT, Branson Ultrasonics Corporation, Danbury, Conn.) for 5 min, to remove excess sulfuric acid. Following sonication, the DI water wash was replaced with fresh DI water and the process was repeated until a neutral pH of 7.0 was verified with pH testing paper, 10 washes ensured that all the sulfuric acid had been removed from the nonwoven. The samples were then air dried overnight.

Material Characterization

To determine the average fiber diameter and evaluate the effectiveness of UV grafting, scanning electron microscopy images were obtained using a Hitachi S-3200N variable pressure scanning electron microscope (VPSEM) (Hitachi High Technologies America, Inc., Schaumberg, Ill.). Nonwoven samples were sputter coated with Pd/Au in argon gas. Images were captured using the microscope with an accelerating voltage of 20 kV at a working distance of 33 mm. The distances across fiber diameters were measured on the SEM micrographs using the Revolution software from 4pi Analysis, Inc. (Hillsborough, N.C.). The average fiber diameter of the 108 I/S PBT and the commercially available PBT nonwovens were determined by measuring the distance across 150 random fibers of the SEM micrographs.

The specific surface areas of the 108 I/S PBT nonwoven after removal of the PLA sea and the commercially available meltblown nonwoven were determined using nitrogen adsorption by the Brunauer, Emmet and Teller (BET) multipoint analysis. One gram of nonwoven material was loaded into a 12 mm sample holder and analyzed on an Autosorb™-1C chemisorption-physisorption analyzer (Quantachrome Industries, Boynton Beach, FLA) measuring 39 nitrogen partial pressure points.

The average pore sizes of the commercially available PBT meltblown nonwoven and the 108 US PBT nonwoven after PLA removal were determined using capillary flow porometry. Nonwoven samples were tested on a CFP-1100-AX capillary flow porometer (Porous Materials Inc., Ithaca, N.Y.). The wetting liquid was Galwick™ (Porous Materials Inc., Ithaca, N.Y.), with a surface tension of 15.9 dynes/cm.

Figure 2:
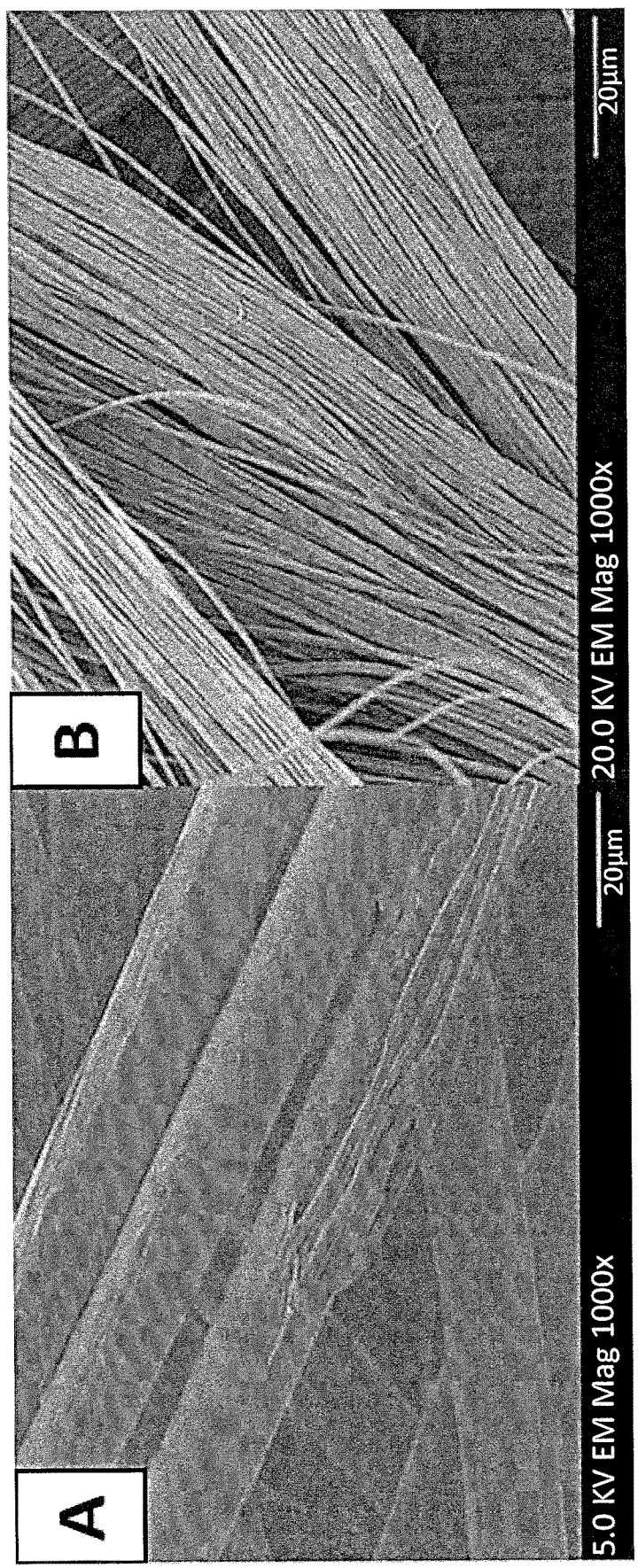
FIGS. 2A and 2B are SEM images of a 108 island I/S PBT nonwoven (A) prior to PLA removal and (B) post PLA removal.

The commercial PBT nonwovens had an average fiber diameter of 3000 nm±900 nm and the 108 I/S PBT nonwovens had an average fiber diameter of 916 nm±174 nm. The specific surface area of the nonwovens was determined using the BET method for nitrogen adsorption. The commercial PBT nonwovens were found to have a specific surface area of 0.86 $m^2/g$ and 108 I/S PBT after PLA removal had a specific surface area of 2.45 $m^2/g$ according to the BET analysis. The average flow pore size was determined using capillary flow porometry. Commercial PBT exhibited a mean flow pore size of 8.73 µm±3.10 µm and the 108 I/S PBT after PLA removal had a mean flow pore size of 8.09 µm±11.9 µm. FIG. 2 shows the 108 I/S PBT before (A) and after (B) removal of the PLA "sea". It can be noticed that the fibers after removal of PLA largely keep their original directional arrangement. This causes the material to have a wide pore size distribution, with the pore structure of the original material being maintained, and the addition of finer pores produced once the PLA is removed.

Static Equilibrium Protein Adsorption at Various Degrees of polyGMA Grafting

Commercially available PBT nonwovens and 108 I/S PBT nonwovens were tested for their equilibrium static protein binding capacity at various degrees of polyGMA coverage in a weak anion exchange format, as well as a strong cation exchange format. Commercially available PBT nonwovens grafted at 2.5, 5.9, 7.2, 12 and 20% weight gains and 108 I/S PBT nonwovens grafted at 5.6, 12, and 20% weight gains were functionalized as weak anion exchangers with DEA. These membranes were challenged with pure BSA as a model protein to establish the static equilibrium binding capacity for these anion exchange membranes. BSA has a molecular weight of 66.5 kDa and an isoelectric point of 4.7 [Sigma Aldrich, St. Louis Mo.]. Approximately 20 mg (25×15 mm) of nonwoven sample was placed in a 3 ml solid phase extraction (SPE) tube and washed with 3 ml of low ionic strength binding buffer, 20 mM Tris HCl pH 7.0, 5 times. Samples were equilibrated for at least 30 min in binding buffer on a rotator (Tissue culture rotator, Glas-col, Terre Haute, Ind.) prior to BSA binding. Once equilibrated 3 ml of 10 mg/ml BSA in 20 mM Tris HCl pH 7.0 were added to each sample and allowed to bind overnight for 15 hours. The low ionic strength buffer at pH 7.0 ensures that the DEA functionalized grafted PBT is positively charged and that BSA is negatively charged to facilitate binding with a minimal amount of ions that would disrupt protein binding. After binding, samples were washed with 3 ml of 20 mM Tris HCl pH 7.0. Five washes with 20 mM Tris HCl pH 7.0 were required to remove all the unbound protein, verified by a negligible amount of protein in the fifth and final wash using UV-Vis spectroscopy at 280 nm. Bound BSA was eluted using a high ionic strength elution buffer, 3 ml of 20 mM Tris HCl pH 7.0+1 M NaCl as the elution buffer. The high concentration of ions in the elution buffer effectively disrupts the ionic interaction, removing the protein from the nonwoven. Elution fractions were collected and protein concentrations were determined using UV-Vis spectroscopy at 280 nm. Static equilibrium binding capacity ($M_{eq}$, in mass of protein per mass of membrane) values were determined using Eq. 2.

$$M_{eq}\left(\frac{mg}{g}\right) = \frac{\text{Protein Concentration}\left(\frac{mg}{ml}\right) \times \text{Volume of Elution Fraction}}{\text{Mass of membrane}} \quad (2)$$

In a similar fashion, strong cation exchange membranes were synthesized by functionalizing grafted PBT nonwovens with phosphate groups. Commercially available PBT meltblown nonwovens grafted at 5.3, 10 and 18% weight gains and 108 I/S PBT nonwovens grafted at 7, 12, and 18% weight gains were functionalized to produce strong cation exchangers. These membranes were challenged with pure polyclonal hIgG as a model protein to establish the equilibrium binding capacity for these cation exchange membranes. Polyclonal hIgG has a molecular weight of 150 kDa and an isoelectric point between 7-9 [Equitek-Bio, Kerrville Tex.]. Approximately 20 mg (25×15 mm) of nonwoven sample were placed in a 3 ml SPE tube and washed with 3 ml low ionic strength binding buffer, 20 mM acetate pH 5.5, 5 times. Samples were equilibrated for at least 30 min in binding buffer on a rotator (Tissue culture rotator, Glas-col, Terre Haute, Ind.) prior to hIgG binding. Once equilibrated, 3 ml of 10 mg/ml hIgG in 20 mM acetate pH 5.5 were added to each sample and allowed to bind overnight for 15 hours. The low ionic strength buffer at pH 5.5 ensures that the phosphoric acid functionalized grafted PBT is negatively charged and that hIgG is positively charged to facilitate binding with a minimal amount of ions that would disrupt protein binding. After binding, samples were washed with 3 ml of 20 mM acetate pH 5.5. Five washes with 20 mM acetate pH 5.5 were required to remove all the unbound protein, verified by a negligible amount of protein in the fifth and final wash using UV-Vis spectroscopy at 280 nm. Bound hIgG was eluted using 3 ml of a high ionic strength elution buffer, 20 mM acetate pH 5.5+1 M NaCl. The high concentration of ions in the elution buffer effectively disrupts the ionic interaction, removing the protein from the nonwoven. Elution fractions were collected and protein concentration was determined using UV-Vis spectroscopy at 280 nm. Eq. 2 was used to calculate the static equilibrium binding capacity.

Kinetics of Protein Adsorption

These experiments were aimed to determine the rate of protein adsorption on grafted ion exchange functionalized nonwoven PBT membranes. In this experiment, commercially available PBT nonwovens and 108 I/S PBT nonwovens were grafted at the same degree of polyGMA coverage (% weight gain), as well as, the same dry polyGMA graft thickness. The dry thickness of the polyGMA graft can be estimated from the % weight gain of polyGMA of the sample and the densities of polyGMA and PBT, assuming that the grafting is both uniform and conformal. These assumptions allow the volumes of the original PBT fiber and the polyGMA graft layer to be treated as concentric cylinders with a cylindrical outer grafted layer surrounding a cylindrical PBT inner core. Using the % weight gain as defined in Eq. 1 with expressions for the outer volume of the cylindrical polyGMA grafted layer and the inner volume of the PBT cylindrical core it is possible to derive an expression for the approximate dry grafted layer thickness ($\delta$) as shown in Eq. 3. A complete derivation of Eq. 3 can be found in the Supplemental Information: Derivation of dry polyGMA graft thickness.

$$\delta = \sqrt{\left(\frac{\% \text{ weight gain}}{100\%}\right) \frac{\rho_{PBT}}{\rho_{polyGMA}} r_1^2 + r_1^2} - r_1 \qquad (3)$$

In Eq. 3, $\delta$ is the dry polyGMA graft thickness, $r_1$ is the average fiber diameter of the specific PBT nonwoven that has been grafted, $\rho_{PBT}$ is the density of PBT polymer (1.30 g/cm$^3$) and $\rho_{polyGMA}$ is the density of dry polyGMA polymer (0.80 g/cm$^3$). Table 1 contains the list of samples produced for the experiments analyzing the influence of contact time on protein binding with their respective % weight gains, dry polyGMA brush thicknesses and type of functionalization.

TABLE 1

PolyGMA grafted nonwovens used in protein adsorption rate studies with specific degrees of grafting, dry graft thickness ($\delta$), and ion exchange functionality.

| Material type | % weight gain | $\delta$ (nm) | Ion exchange function |
|---|---|---|---|
| Commercial PBT | 20 | 227 | Anion exchange |
| Commercial PBT | 5.9 | 70 | Anion exchange |
| 108 I/S PBT | 20 | 69 | Anion exchange |
| Commercial PBT | 18 | 205 | Cation exchange |
| Commercial PBT | 5.3 | 63 | Cation exchange |
| 108 I/S PBT | 18 | 63 | Cation exchange |

Approximately 20 mg (25×15 mm) of nonwoven sample was placed in a 3 ml SPE tube and washed extensively with binding buffer, 20 mM Tris HCl pH 7.0 for anion exchange experiments with BSA, or 20 mM acetate pH 5.5 for cation exchange experiments with hIgG. Samples were equilibrated for at least 30 min in binding buffer on a rotator (Tissue culture rotator, Glas-col, Terre Haute, Ind.) prior to protein binding. Once samples were equilibrated they were challenged with either 3 ml of 10 mg/ml BSA or 3 ml of 10 mg/ml hIgG for anion exchange or cation exchange nonwovens respectively. Protein was allowed to bind at various exposure times between 30 seconds to 15 hours. After binding, anion exchange samples that had bound BSA were washed five times with 3 ml of 20 mM Tris HCl pH 7.0 and cation exchange samples that bound hIgG were washed five times with 3 ml of 20 mM acetate pH 5.5 to remove any unbound protein. The BSA was eluted using 3 ml of the high ionic strength elution buffer, 20 mM Tris HCl pH 7.0+1 M NaCl. The hIgG was eluted using 3 ml of the high ionic strength elution buffer, 20 mM acetate pH 5.5+1 M NaCl. The elution fractions were analyzed using UV-Vis spectroscopy at 280 nm and the amount of protein bound for each material was calculated using Eq. 2.

Grafting of PBT Nonwovens

Commercial PBT and 108 I/S PBT nonwovens were successfully grafted with various degrees of polyGMA coverage. The results for the degree of grafting at increasing UV exposure times are presented in FIG. 3.

Figure 3:
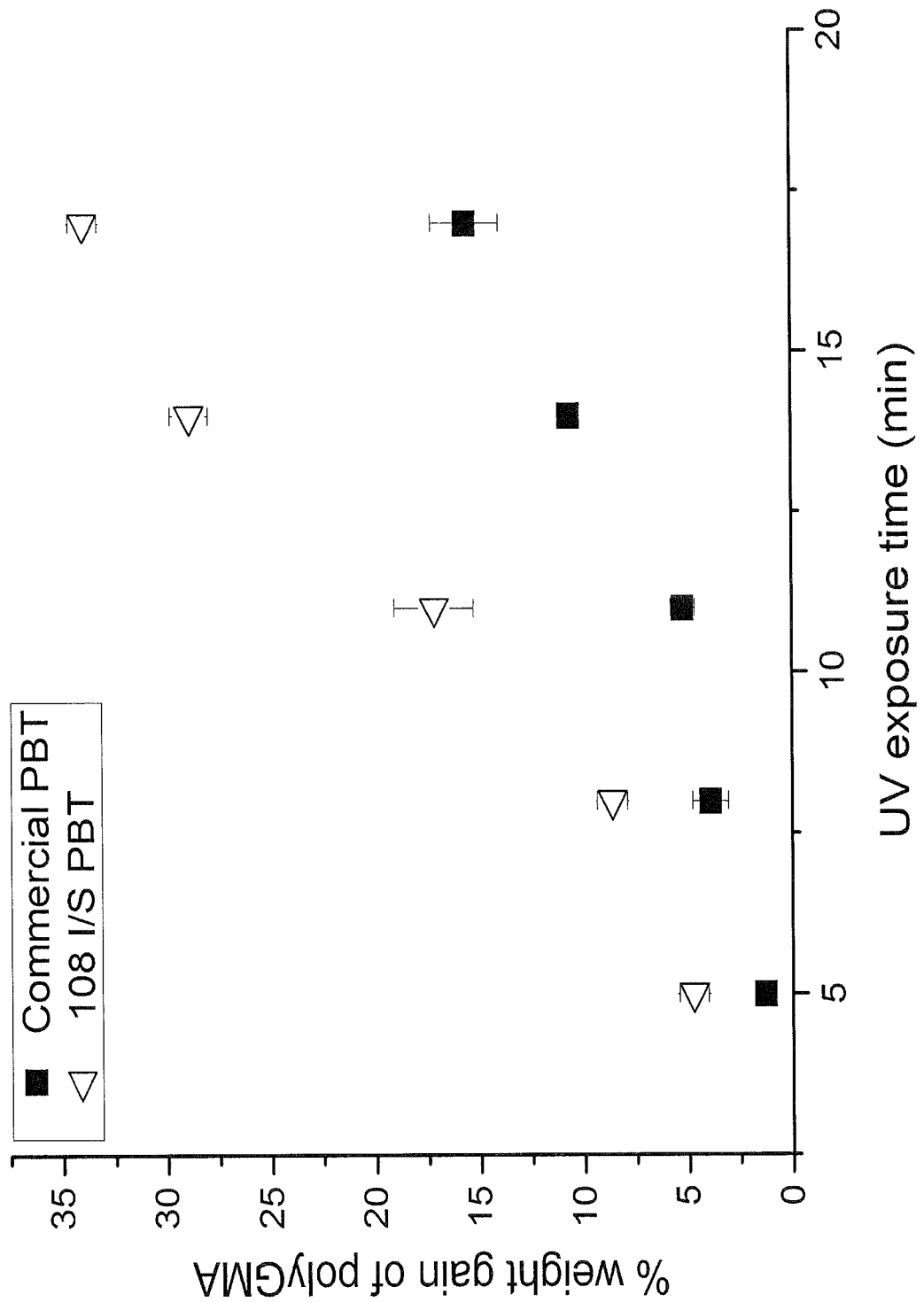
FIG. 3 illustrates the extent of polyGMA grafting at various UV exposure times for a commercial PBT nonwoven and the 108 I/S nonwovens after PLA removal.
Figure 4:
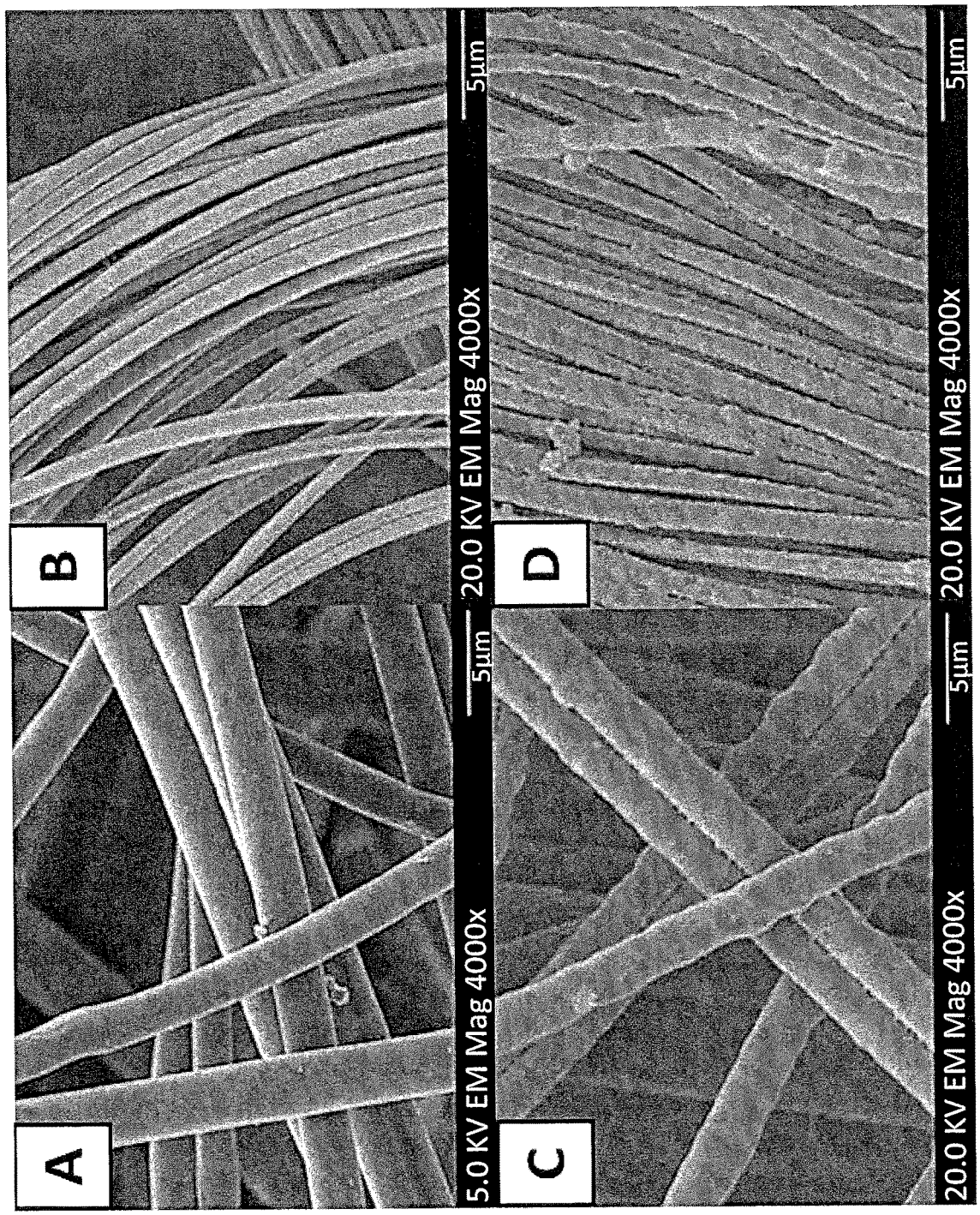
FIGS. 4A-4D are SEM images of (A) a commercial PBT nonwoven prior to grafting, (B) a 108 I/S PBT nonwoven prior to grafting, (C) a commercial PBT nonwoven grafted to 20% weight gain, and (D) a 108 I/S PBT nonwoven grafted to 20% weight gain.

From FIG. 3, it is apparent that the 108 I/S PBT nonwovens graft at a faster rate than the commercial PBT nonwovens. Compared to the commercial PBT nonwovens, the 108 I/S PBT nonwovens have 2.85 times more available area for initiation of GMA polymerization, resulting in approximately a 2.4 times higher rate of grafting. Both nonwovens exhibit complete conformal and uniform polyGMA graft coverage at different minimum degrees of grafting: above 3% weight gain for the commercial PBT meltblown nonwoven and above 6% weight gain for 108 I/S PBT nonwoven. SEM images of the 108 I/S PBT nonwoven and the commercial PBT nonwoven before and after grafting at 20% weight gain are presented in FIG. 4.

FIGS. 4C and 4D display a visible increased roughness on the surface of the PBT fibers attributed to polyGMA grafting that is not present in FIGS. 4A and 4B for the ungrafted PBT nonwovens. In addition to increasing the rate of polyGMA grafting, the smaller diameters of the 108 I/S fibers have a significant impact on the thickness of the grafted layer. In FIGS. 4C and D both the commercial PBT and the 108 US PBT have the same 20% weight gain of polyGMA grafting. However, there is more available surface area to graft in a given sample of the 108 I/S nonwoven, resulting in a thinner grafted layer thickness than in a commercial PBT nonwoven. The actual dry graft thickness for various degrees of grafting on commercial PBT and 108 I/S PBT were calculated using Eq. 3 and presented in Table 1. A visual schematic comparing the dry polyGMA graft thickness for commercial PBT and 108 I/S PBT grafted at 20% weight gain and commercial PBT grafted at 5.9% weight gain are presented in FIG. 5.

Figure 5:
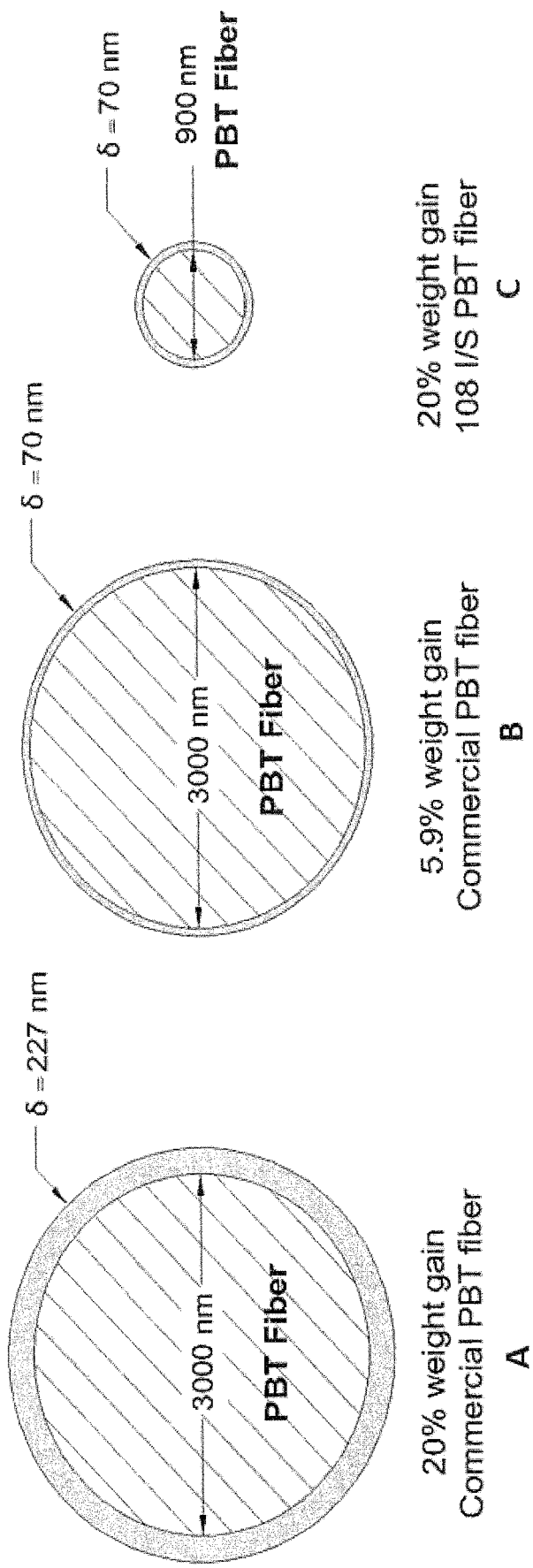
FIGS. 5A-5C are cross-sectional schematic views of the fiber diameter and dry graft layer thicknesses of (A) a commercial PBT grafted to 20% weight gain, (B) a commercial PBT nonwoven grafted to 5.9% weight gain, and (C) a 108 I/S PBT nonwoven grafted to 20% weight gain.

The visual representations in FIG. 5 illustrate how a thicker polyGMA graft layer is required to achieve 20% weight gain on commercial PBT nonwovens (FIG. 5A) compared to 108 I/S PBT nonwovens (FIG. 5C) for the same % weight gain of grafting. It can also be seen that in order for the grafted commercial PBT nonwoven to have the same grafted layer thickness as an I/S PBT nonwoven, the % weight gain of the commercial PBT needs to be over three times smaller than that of the I/S grafted nonwoven (compare FIG. 5B to FIG. 5C). As will be seen subsequently, the grafted layer thickness controls the rate of adsorption of protein to the membrane. However, the equilibrium binding capacity is only a function of the % weight gain.

Equilibrium Protein Binding Ion Exchange Capacity of Derivatized PBT Nonwovens

Commercial PBT nonwovens and 108 I/S nonwovens were grafted at various % weight gains and their equilibrium protein binding capacities for both anion exchange capture of BSA and cation exchange capture of hIgG were determined. The results of these experiments are shown in FIG. 6.

Figure 6:
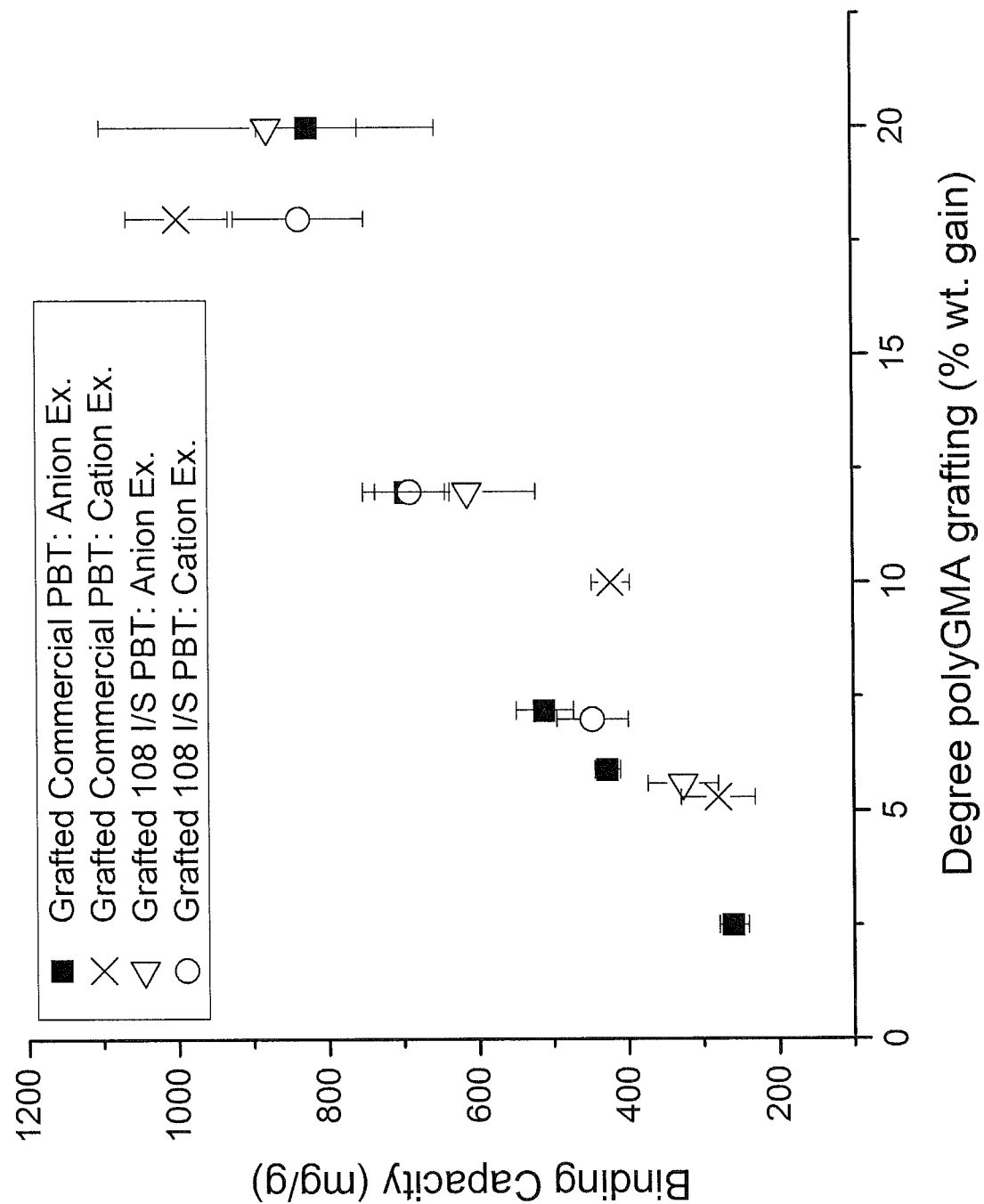
FIG. 6 illustrates the equilibrium binding capacity for 108 I/S PBT nonwovens and commercial PBT nonwovens grafted at various degrees and functionalized either to be a cation or anion exchanger to bind IgG and BSA, respectively.

The results of FIG. 6 show that equilibrium protein binding capacity increases linearly with increased degree of polyGMA grafting (% weight gain), for both anion and cation exchange membranes and for proteins of two very different molecular weights and sizes. The 108 I/S PBT nonwovens have 2.85 times more specific surface area than the commercial PBT nonwovens yet they both achieved very similar equilibrium binding capacities. These results indicate that, given enough time, both a medium sized protein like BSA (66.5 kDa) and a large protein like hIgG (150 kDa) are able to penetrate into the grafted layers of the sample until the entire grafted layer is saturated with protein. Even though these proteins have much different molecular weights, BSA and hIgG have similar specific volumes (0.733 $cm^3/g$ and 0.739 $cm^3/g$ respectively). When both the commercial PBT nonwoven and the I/S PBT nonwoven samples have the same original mass and the same % weight gain they have the same mass of grafted layer, and therefore it is not hard to understand how the equilibrium protein binding capacity on a mass basis would be the same. These results also indicate that the grafted layers under the binding solution conditions used in this experiment must be either flexible or porous enough to allow penetration of even a large molecule like hIgG which has a radius of gyration of 100 nm. Since these grafted layers are highly charged, during binding conditions at low ionic strengths the grafted layers are likely in an extended configuration, allowing protein penetration.

It is also important to note that for the high % weight gain samples the equilibrium protein binding capacities are extremely large, reaching values of over 800 mg of bound protein per gram of nonwoven at 20% weight gain. If the BSA and hIgG were adsorbing to the outer surface of the fibers only, and not penetrating into the grafted layer, the binding capacities would be much lower. Monolayer adsorption of BSA and hIgG have been reported to be somewhere in the range of 2.5-6 $mg/m^2$ and 2-5.5 $mg/m^2$ respectively. Given these monolayer coverage numbers and the measured specific surface area of the commercial PBT nonwovens, the monolayer binding capacity for BSA and hIgG would be 5.2 and 4.7 mg/g respectively. Similarly, the maximum monolayer coverage of BSA and hIgG on the 108 I/S PBT nonwovens would be 14.7 and 13.5 mg/g respectively. All of the equilibrium binding capacities reported in FIG. 6 are between 50 and 200 times greater than monolayer protein adsorption. This is very strong evidence that the polyGMA brushes created a 3-dimensional binding environment, where equilibrium protein adsorption scales with the amount of polymer brush available for binding per mass of membrane. FIG. 6 shows that both nonwovens with the same extent of polyGMA grafting exhibit the same equilibrium protein binding capacity. For instance at 20% weight gain the commercial PBT nonwovens captured 823±66 mg/g of BSA at equilibrium and the 108 I/S PBT nonwovens with 20% weight gain captured 817±164 mg/g of BSA by anion exchange. FIG. 5 shows that the 20% weight gain polyGMA dry graft thickness is larger for the commercial PBT nonwovens (δ=227 nm) than the 108 I/S PBT nonwovens (δ=69 nm). The % weight gain determines the equilibrium binding capacity however the distribution of protein at equilibrium is very different between the commercial PBT nonwovens and the 108 I/S PBT nonwovens. At equilibrium, protein is distributed in a thinner layer over a larger surface area for the 108 I/S PBT nonwovens compared to the commercial PBT nonwovens that require a thicker polyGMA grafted layer to bind the same amount of protein due to the lower specific surface area of the material.

Rates of Adsorption to polyGMA Grafted Anion and Cation Exchange Nonwovens

Figure 7:
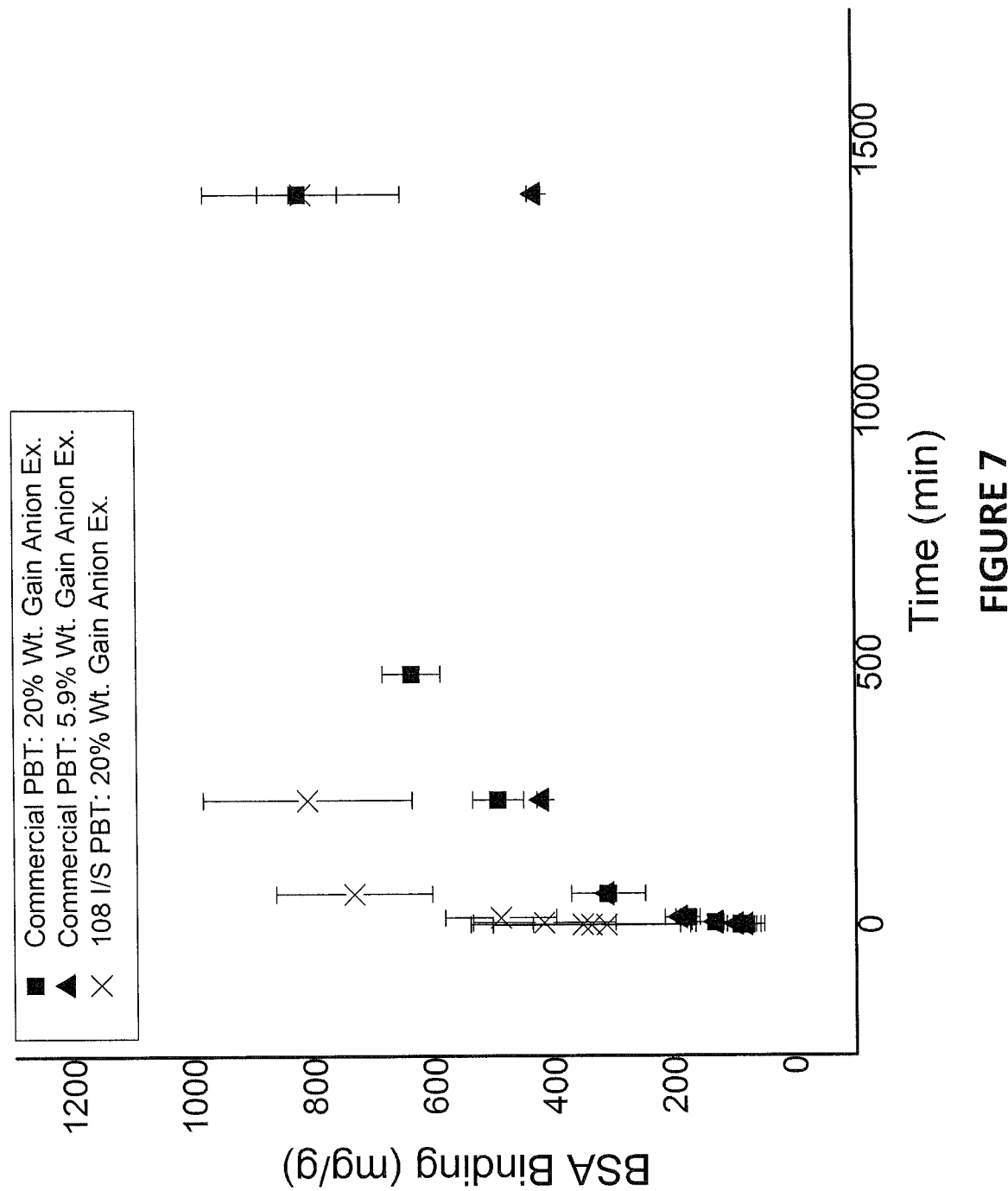
FIG. 7 illustrates BSA capture at various contact times for anion exchange functionalized grafted nonwovens: commercial PBT grafted at 20% and 5.9% weight gain, as well as 108 I/S PBT grafted at 20% weight gain.

In section 3.3 it was shown that ion exchange functionalized polyGMA grafted nonwovens exhibit very high equilibrium binding capacities. However, for some applications it is necessary to understand the effects of % weight gain and grafted layer thickness on the kinetics of protein adsorption to the polyGMA brush layers. FIG. 7 displays the results for BSA capture by anion exchange at various protein exposure times for commercially grafted PBT at 20% and 5.9% wt. gain, as well as, 108 I/S grafted PBT at 20% wt. gain. These degrees of grafting were chosen because, at 20% weight gain both the commercial PBT and the 108 I/S PBT have the same amount of polyGMA grafting and equilibrium binding capacity displayed in FIG. 6 and commercial PBT grafted at 5.9% grafting has the same polyGMA graft thickness as the 108 I/S PBT as can be seen in FIG. 5, and should have similar rates of protein adsorption. The 108 I/S grafted at 5.9% weight gain was not investigated because it is at the lower limit of grafting necessary to give complete conformal grafting and would result in high variability in the material tested for protein binding.

These experiments were done in batch, under static or non-flow conditions. In FIG. 7 the rate of adsorption of BSA to commercially available PBT and 108 I/S PBT nonwovens grafted to the same extent of polyGMA grafting at 20% weight gain were compared for protein capture at various contact times. At 20% weight gain both the commercial PBT nonwovens and the 108 I/S PBT nonwovens converge to the same binding capacity (~800 mg/g) given sufficient contact time, consistent with the results shown previously. However, it can be seen that BSA adsorbs to the 20% weight gain grafted commercial PBT nonwovens at a much slower rate than to the 108 I/S PBT nonwovens. After 4 hours the 108 I/S PBT nonwovens grafted at 20% weight gain had already reached its equilibrium binding capacity, compared to the commercial PBT nonwovens grafted at 20% weight gain that had only reached 60% of the equilibrium binding capacity. FIG. 7 also shows that the commercial PBT nonwoven grafted at 5.9% weight gain had also achieved its equilibrium binding capacity after 4 hours of protein contact time. The 108 I/S PBT nonwovens grafted to 20% weight gain and the commercial PBT nonwovens grafted to 5.9% weight gain have the same dry polyGMA graft thickness of 70 nm according to Eq. 3 and as depicted in FIG. 5. This is good evidence that the rate of adsorption of proteins by ion exchange to these grafted nonwoven fabrics is largely determined by the diffusional limitations through the grafted layer, and thus dominated by the grafted layer thickness, which is in turn determined by the initial fiber diameter of the nonwoven and the % weight gain of grafted material.

Figure 8:
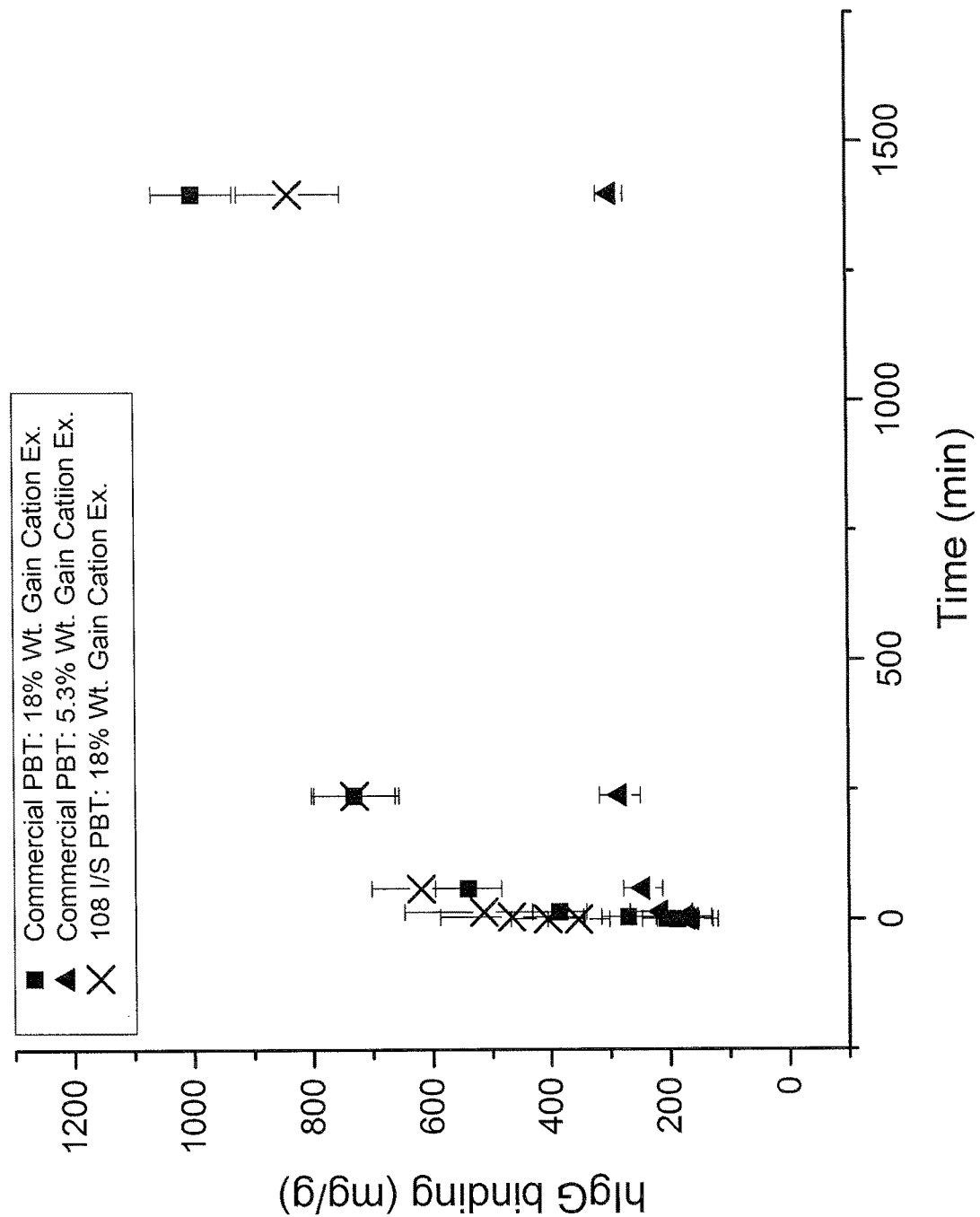
FIG. 8 illustrates hIgG adsorption at various contact times for cation exchange functionalized grafted nonwovens: commercial PBT grafted at 18% and 5.3% weight gain, as well as 108 I/S PBT grafted at 18% weight gain.

The kinetics of hIgG adsorption by cation exchange to grafted commercial PBT nonwovens and 108 US PBT nonwovens were also investigated. FIG. 8 displays the results for hIgG capture at various contact times for commercially grafted PBT at 18% and 5.3% wt. gain, as well as 108 I/S grafted PBT at 18% wt. gain cation exchangers.

FIG. 8 shows how commercial PBT nonwovens and 108 I/S PBT nonwovens grafted to the same extent of polyGMA grafting, 18% weight gain, converge to similar equilibrium hIgG binding capacities when functionalized as cation exchangers. This is the same behavior shown in FIG. 7 for anion exchange membranes. The 108 I/S PBT nonwoven sample grafted to 18% weight gain reached equilibrium binding after 4 hours compared to the commercial PBT nonwoven grafted at 18% weight gain that required a full day of protein contact. The commercial PBT nonwovens with 5.3% weight gain, grafted to the same graft thickness ($\delta$=63 nm) as the 108 I/S PBT nonwovens grafted with 18% weight gain also reached equilibrium in approximately 4 hours. Again, these results are totally analogous to the results found for anion exchange nonwovens in FIG. 7, providing further proof that the kinetic phenomena being observed are not dependent on the grafted layer charge type, or the size of the protein being adsorbed.

Figure 9:
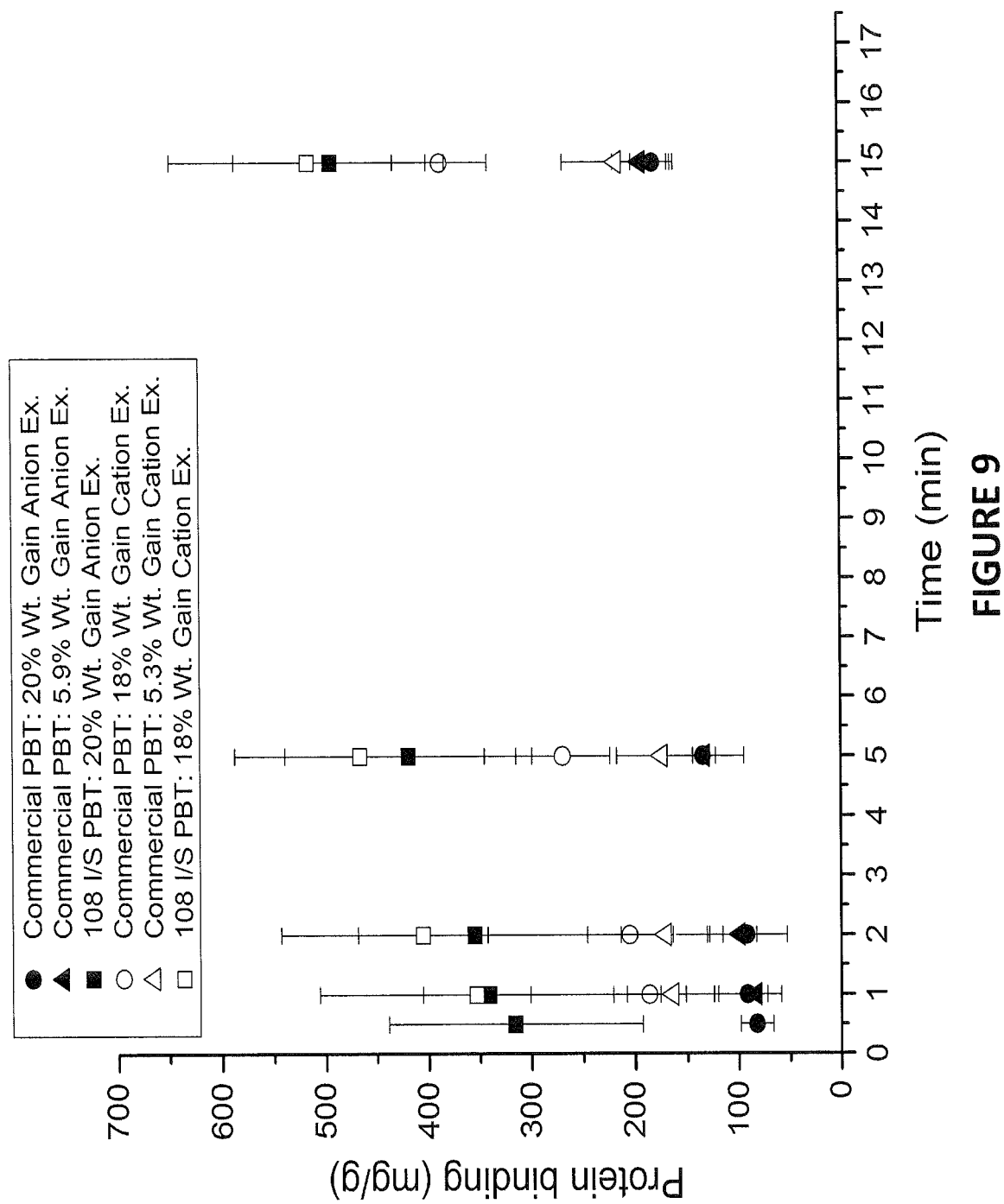
FIG. 9 illustrates protein binding for contact times 15 min or less, for all of the ion exchange functionalized grafted nonwovens that were tested for BSA and hIgG binding rates.

For practical applications it is important to evaluate how protein binds at short residence times. For example, if these membranes are to be used for protein capture in downstream purification of biologics, it would be desirable for the residence time in the adsorption device to be 5 minutes or less. FIG. 9 shows the protein binding data in FIGS. 7 and 8 for the anion and cation exchange grafted nonwovens discussed above for BSA and hIgG contact times under 15 min.

In FIG. 9 it is apparent that the grafted 108 I/S PBT nonwovens are capable of binding more protein at very short contact times in both cation and anion exchange mode than any of the functionalized grafted commercial PBT nonwovens. The ability of the 108 I/S PBT nonwovens to bind more protein initially is due to the higher specific surface area of the fabric. Recall that the specific surface area of the I/S PBT nonwoven after PLA removal is 2.85 times larger than the specific surface area of the commercial meltblown PBT nonwoven. The data present in FIG. 9 was extrapolated to time t=0 to estimate the initial amount of protein bound ($M_i$) that occurred instantaneously due adsorption of protein on the nonwovens surface area before any diffusion into the polyGMA layer has occurred. The initial amounts of protein adsorption are given in Table 2.

TABLE 2

Initial amount of protein adsorbed ($M_i$) due to surface area adsorption.

| Sample | Initial amount of protein binding ($M_i$) (mg/g) |
|---|---|
| Commercial PBT: 20% Wt. Gain Anion Ex. | 76 |
| Commercial PBT: 5.9% Wt. Gain Anion Ex. | 73 |
| 108 I/S PBT: 20% Wt. Gain Anion Ex. | 311 |
| Commercial PBT: 18% Wt. Gain Cation Ex. | 165 |
| Commercial PBT: 5.3% Wt. Gain Cation Ex. | 163 |
| 108 I/S PBT: 18% Wt. Gain Cation Ex. | 338 |

If the results presented in Table 2 are averaged for the functionalized commercial PBT nonwovens (120 mg/g average initial protein binding) and the 108 I/S PBT nonwovens (325 mg/g average initial protein binding) it is observed that the 108 I/S PBT nonwovens bind 2.7 times more protein initially than the commercial PBT nonwovens. This is in close agreement with the 2.85 times higher experimental surface area for the 108 I/S PBT nonwovens than the commercial PBT nonwovens. For this reason it becomes advantageous to use the grafted 108 I/S PBT nonwovens when very short residence times are required because they can achieve fairly high binding capacities strictly due to higher specific surface area.

The results of the adsorption rate measurements for both cation and anion exchange grafted nonwovens indicate that the adsorption process is diffusion limited in these functionalized polyGMA brush matrices, requiring several hours to reach equilibrium. To minimize these diffusional challenges higher surface area (smaller fiber diameter) nonwoven fabrics result in thinner grafted layer thicknesses for the same % weight gain compared to lower surface area (larger fiber diameter) materials, as shown in FIG. 5. The thinner polyGMA layer reduces the diffusion distance and shortens the time to reach equilibrium while maintaining high equilibrium binding capacities as seen in FIGS. 7 and 8. In addition to reducing the time to reach equilibrium for specific degrees of polyGMA grafting the higher specific surface area 108 I/S PBT nonwovens also contributes to a higher initial amount of protein adsorption as observed in FIG. 9. The overall equilibrium protein binding capacity will be determined by the degree of polyGMA grafting but the effective rates of protein capture are determined by the initial specific surface area of the nonwoven and the thickness of the polyGMA brush layer.

Model for the Kinetics of Protein Adsorption to Grafted polyGMA Nonwoven Samples The insights provided by the results of both the equilibrium and rate measurements for protein adsorption to the anionic and cationic grafted layer nonwovens described above suggest that it may be possible to develop a mathematical model to describe the adsorption process, and that this mathematical model should be qualitatively and quantitatively consistent with the experimental results. The rate of adsorption of a charged protein to a charged binding site is nearly instantaneous compared to the rate of mass transfer limitations in ion exchange media. It has already been proposed that in the case of diffusion into functionalized polymer layers the rate-determining step for protein adsorption is the penetration into the polymer layer. A cross sectional illustration of how protein adsorbs over time to the functionalized polyGMA brush layer grafted around a PBT fiber is presented in FIG. 10.

Figure 10:
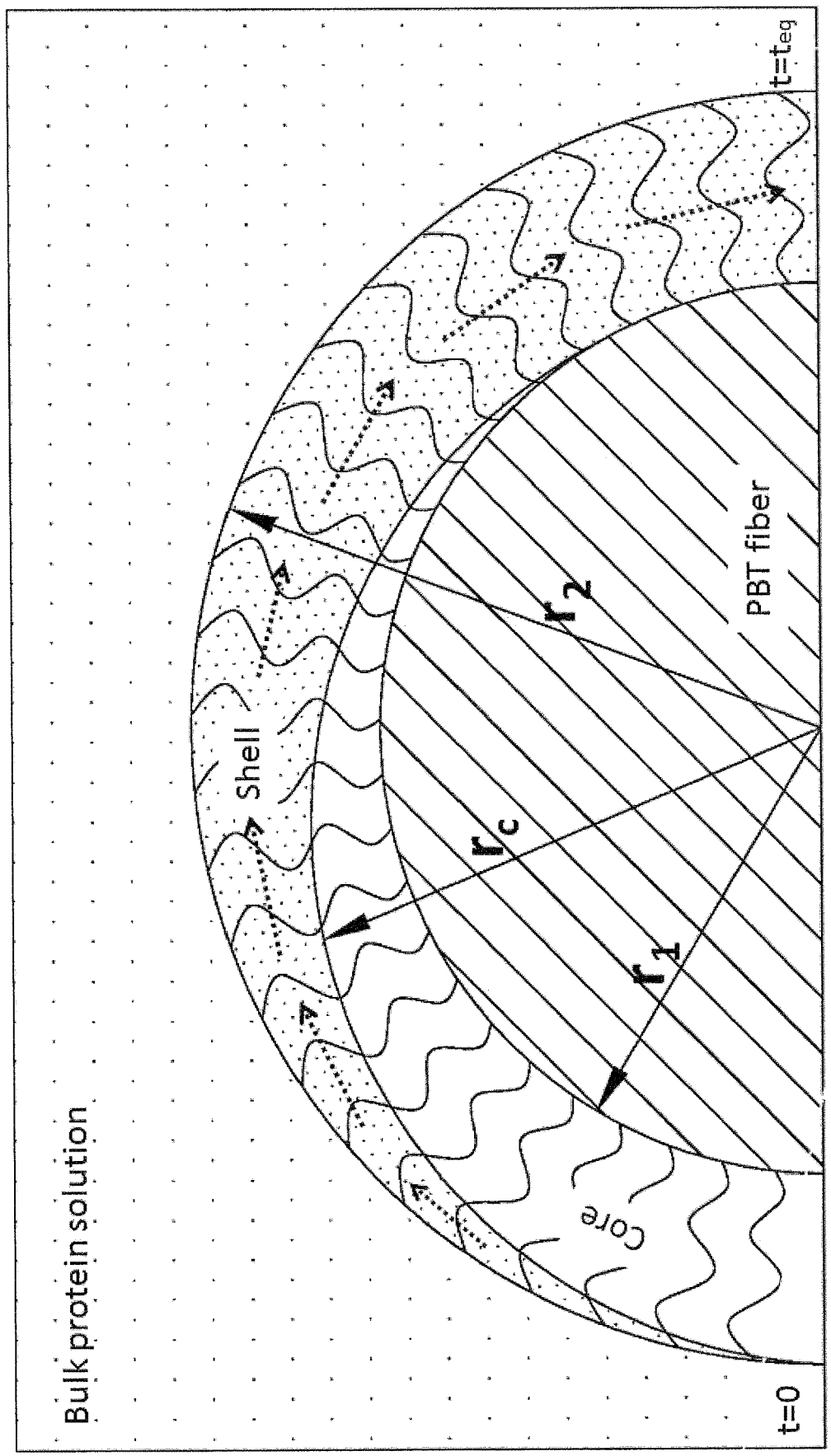
FIG. 10 is a cross-sectional schematic view of a grafted PBT fiber filling with protein over time, converting an available polyGMA "core" into a saturated protein/polyGMA shell as time (t) progresses, $r_1$=PBT fiber radius, $r_c$=core radius, $r_2$=grafted fiber radius.

Because the rate of adsorption to the grafted layer is likely to be much faster than the rate of diffusion of protein through the layer, it is not unreasonable to theorize that once a protein molecule is bound to charged groups on the outer surface of the grafted layer, additional molecules entering the grafted layer will have to diffuse through the layer containing the bound proteins. Once the unbound protein diffuses through the bound protein layer and encounters free charged groups on the polymer it will bind immediately and the bound protein layer will grow with time until it reaches the surface of the PBT fiber. The phenomenon just described is consistent with the traditional shrinking core model that has been applied to the diffusion of proteins in chromatographic resins. The bound protein on the polyGMA grafted layer can be viewed as forming a "shell" that creates a significant diffusional resistance for protein mass transport into the remaining layer of unbound polyGMA. FIG. 10 shows how the thickness of the shell increases over time until the entire polyGMA brush layer has bound protein. The unbound polyGMA brushes are the "core" in this model that shrinks as protein penetrates the "shell" and binds to the brushes. Initially the thickness of the "shell" with adsorbed protein will be zero and the rate of adsorption of protein to the outer surface will be very fast. As time progresses the "shell" thickness and the diffusional resistance to mass transfer increase until the adsorbed protein shell reaches the surface of the PBT and the "core" shrinks to zero. We also assume that, because the diffusion process is slow relative to the rate of adsorption, the diffusion process is in a quasi-steady state so that the rate of protein transport by diffusion into the polyGMA brush layer is constant with position, so that at any point in the shell the rate of adsorption of protein to the charged polymer is equal to the rate of diffusion through the shell. With these assumptions, at any radial position within the grafted layer, the rate of adsorption of protein is equal to the rate of radial diffusion of protein into the polyGMA brush layer, expressed by Eq. 4.

$$R_a = D_e \frac{\partial C_{protein}}{\partial r}(2\pi r L) \qquad (4)$$

In Eq. 4, $R_a$ is the total rate of adsorption of protein to the shell at a given radial position, $D_e$ is the effective diffusivity of protein in the polyGMA brush matrix with adsorbed protein, $C_{protein}$ is the protein concentration that is diffusing through the polyGMA layer, L is the length of a given fiber, and r is the radial position. Since the rate of protein binding by the polyGMA brushes is nearly instantaneous then the concentration of protein at the interface between the "core" and the "shell" ($r=r_c$) can be taken to be zero. Additionally, since diffusion through the shell is the rate-limiting step the concentration of protein at the exterior of the shell ($r=r_2$) is the equivalent to that of the bulk protein concentration in solution, denoted as $C_{bulk}$. Integrating Eq. 4 from the inner to the outer radius of the grafted layer leads to an expression for the radial variation in the rate of adsorption of protein, $$R_a = \frac{D_e(2\pi L)C_{bulk}}{\ln\left(\frac{r_2}{r_c}\right)} \quad r_1 < r_c < r_2 \qquad (5)$$

The rate of protein diffusing into the core and binding to the polyGMA is equal to the mass rate of consumption of polyGMA "core" material available for binding $$R_a = R_c \qquad (6),$$

The rate of disappearance of mass of unoccupied polyGMA "core" can be expressed in terms of the density and the time rate of change of volume occupied by the polyGMA (Eq. 7), $$R_c = -\rho_{core}(2\pi r_c L)\frac{dr_c}{dt} \qquad (7)$$

Substitution of Eqs. 6 and 7 into Eq. 5 yields an equation for the time rate of change of the interface between the "core" of polyGMA and the "shell" with bound protein, $$-\rho_{core}(2\pi r_c L)\frac{dr_c}{dt} = \frac{D_e(2\pi L)C_{bulk}}{\ln\left(\frac{r_2}{r_c}\right)} \qquad (8)$$

At time t=0, the core radius is $r_2$. Integration of Eq. 8 with respect to time leads to an expression for the mass adsorbed into the grafted layer as a function of time, $$\Psi = \frac{t}{\tau} = \frac{1}{2} \qquad (9)$$

$$\left(\frac{M - M_i}{M_{eq} - M_i}\right) + \left[\frac{1}{1 - \phi^2} - \frac{M - M_i}{M_{eq} - M_i}\right]\ln\sqrt{1 - \left(\frac{M - M_i}{M_{eq} - M_i}\right)(1 - \phi^2)}$$

In Eq. 9 M is the mass of protein bound at any given time, $M_{eq}$ is the mass of protein bound at equilibrium and $M_i$ is the initial mass of protein bound at time t=0 due to adsorption on the external surface area of the nonwovens. The shrinking core model does not predict this initial protein adsorption ($M_1$) but it can be estimated from our experimental results (see FIG. 9). When using this model, the fraction of the equilibrium amount of protein adsorbed to the polyGMA brush layer as a function of time after this initial immersion step in solution is given by $\Psi=[(M-M_i)/(M_{eq}-M_i)]$. The total amount of protein bound to the polyGMA brush layer as a function of time is dependent on two parameters: $\tau$ and $\phi$ which vary for each different nonwoven with different fiber diameter and grafted layer thickness, $$\tau = \frac{(r_2^2 - r_1^2)\rho_{core}}{2D_eC_{bulk}} \qquad (10)$$

$$\phi = \frac{r_1}{r_2} \qquad (11)$$

In Eq. 10 and 11, $r_1$ and $r_2$ are the radii of the PBT fiber and the fiber covered with the polyGMA brush layer respectively as can be seen in FIG. 10. Additionally in Eq. 10, $D_e$ is the effective diffusivity for protein through the shell layer, and $C_{bulk}$ is the concentration of protein solution in the liquid phase, which was 10 mg/ml for each experiment performed.

It is known that polyGMA brushes swell in aqueous solvents when functionalized with charged groups as a result of electrostatic repulsion between the charges. Therefore, the dry polyGMA brush thickness calculated by Eq. 3 cannot be used to determine $r_2$ and a swollen polyGMA brush thickness must be calculated. If we assume that polyGMA brushes are completely extended when the brush layer is completely filled with protein we can estimate the polyGMA brush thickness $r_2$. This is a reasonable assumption because proteins are known to achieve a high packing efficiency in polyelectrolyte brush matrices when given sufficient time. The mass of protein adsorbed per mass of the membrane at equilibrium is $M_{eq}$ (mass protein/mass membrane) and is the equivalent to the binding capacity of the material. The mass of protein bound can be converted to the volume of protein bound using the partial specific volume of the protein. The volume occupied by protein is that of an annular cylinder around the PBT fiber. Using this geometry, $r_2$ can be calculated to give the swollen polyGMA brush thickness using Eq. 12. The derivation of Eq. 12 can be found in the Supplementary Information: Derivation of swollen polyGMA brush radius.

$$r_2 = \sqrt{M_{eq} \bar{v} \rho_{PBT} r_1^2 + r_1^2} \quad (12)$$

In Eq. 12, $M_{eq}$ is the equilibrium binding capacity, $\bar{v}$ is the partial specific volume of protein ($\bar{v}_{BSA}=0.733$ cm³/g and $\bar{v}_{IgG}=0.739$ cm³/g), $\rho_{PBT}$ is the density of PBT fibers ($\rho_{PBT}=1.33$ g/cm³), and $r_1$ is the radius of the PBT fibers.

In addition to increasing the observed brush thickness, the swelling of the polyGMA brushes effectively increases the volume the brushes occupy resulting in a decreased observed density for the "core". The unbound swollen polyGMA brushes make up the "core" and the density of these brushes is the density of the core. We know the mass of the polyGMA brushes from the weight gain on the PBT nonwovens and we can calculate the volume of the swollen polyGMA brushes using the calculated values for $r_2$. The mass and the volume for the polyGMA brushes can be used to calculate an effective density of the "core" that is expressed by Eq. 13, the derivation can be found in the Supplementary Information: Derivation of polyGMA core density.

$$\rho_{core} = \frac{\frac{\% \text{ weight gain}}{100\%} \rho_{PBT} r_1^2}{r_2^2 - r_1^2} \quad (13)$$

In Eq. 13, $\rho_{core}$ is the effective density of the "core" that protein adsorbs to, the % weight gain is the mass of polyGMA added to the nonwoven from grafting, $\rho_{PBT}$ is the density of the PBT fibers, $r_1$ is the radius of the PBT fibers and $r_2$ is the swollen polyGMA radius. The calculated values for $r_2$ as well as the subsequent swollen polyGMA brush thicknesses, the effective core densities, and the values for $\phi$ are presented in Table 3.

values of the effective diffusivity of the proteins diffusing through the "shell" of protein adsorbed to the polyGMA grafted layer.

Figure 11:
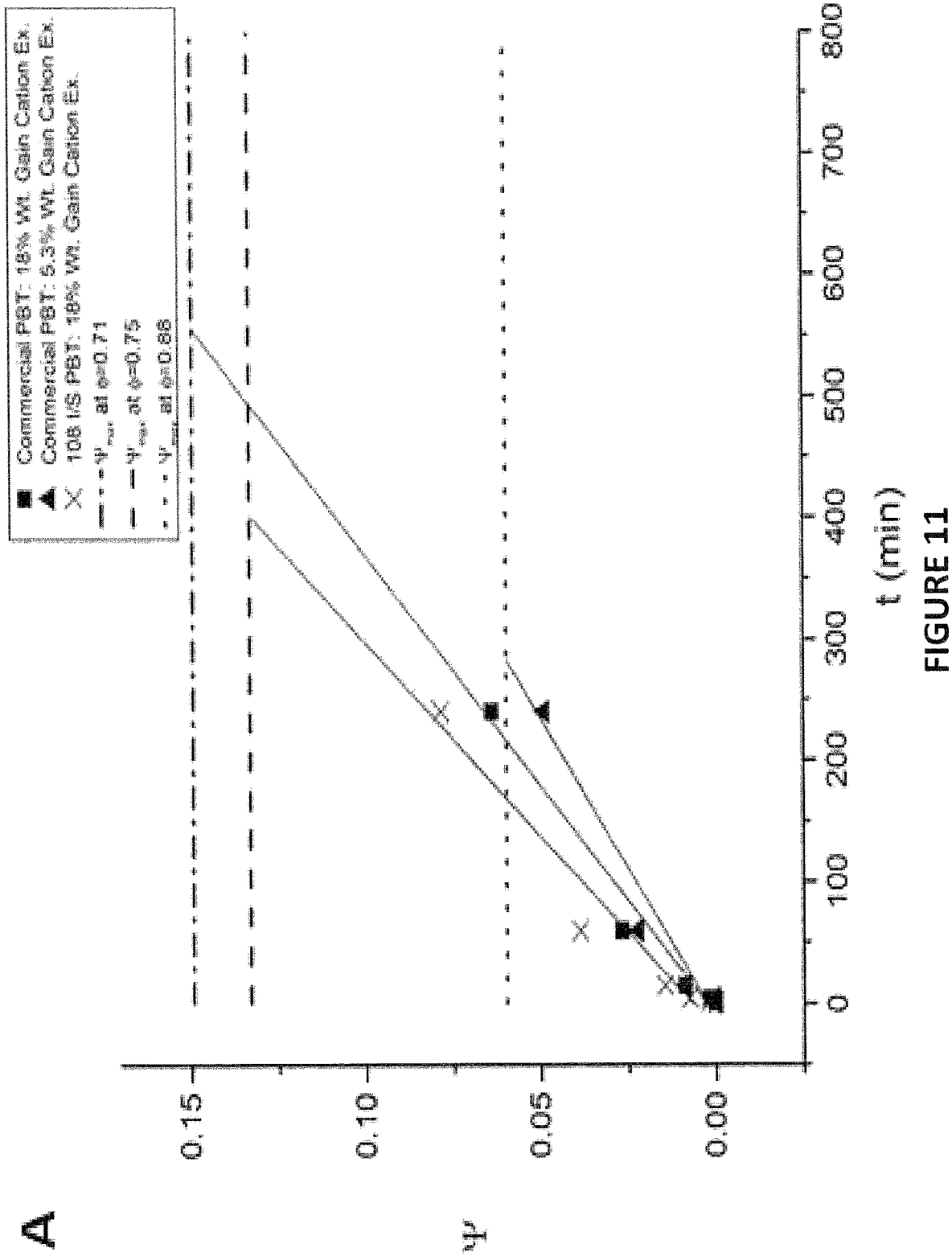
FIGS. 11A and 11B illustrate (A) Ψ values calculated from experimental data for the conversion of the anion exchange functionalized polyGMA nonwovens plotted vs. time with lines of best fit and (B) values calculated from experimental data for the conversion of the cation exchange functionalized polyGMA nonwovens plotted vs. time with lines of best fit.
Figure 11:
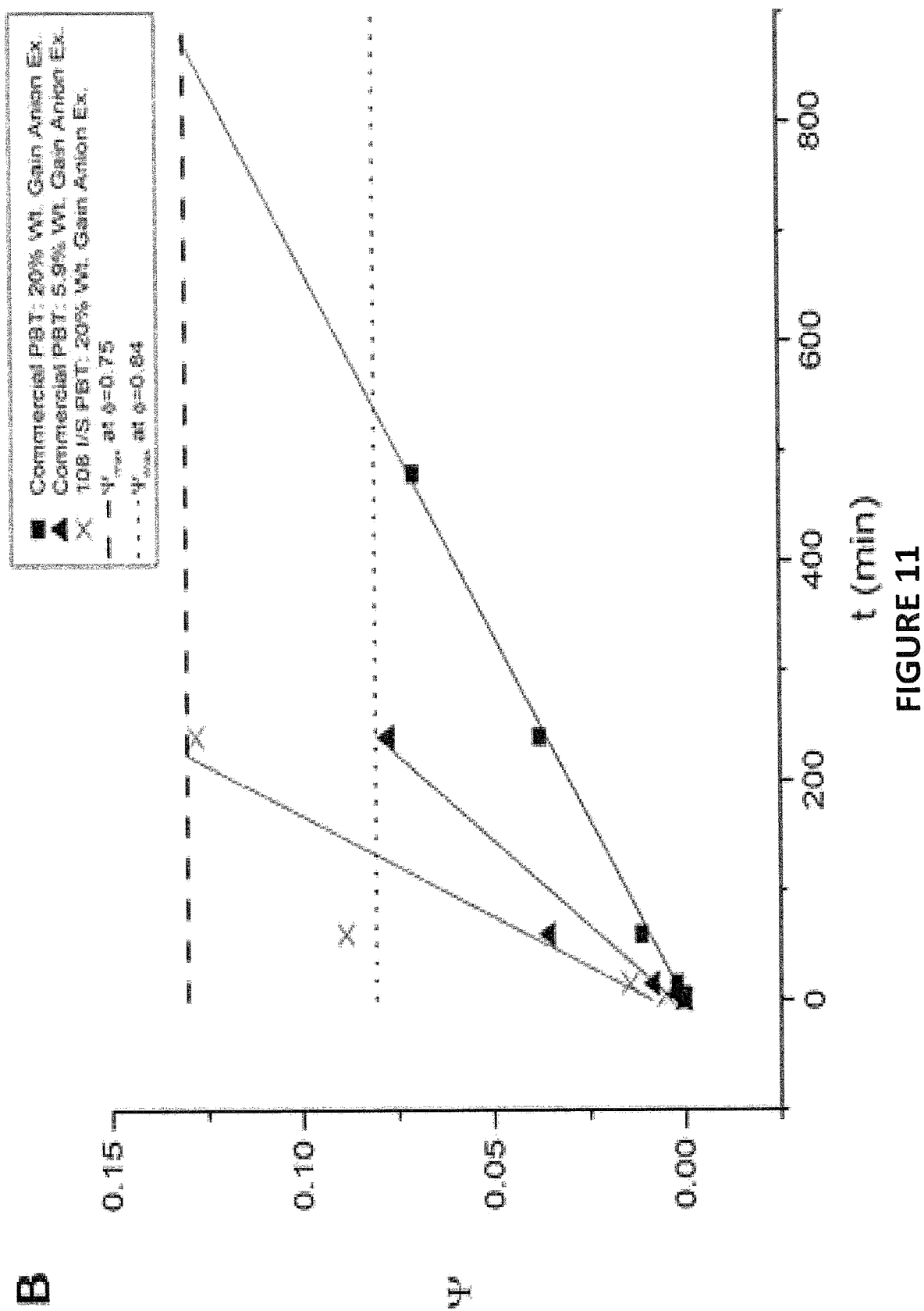
Figure 13:
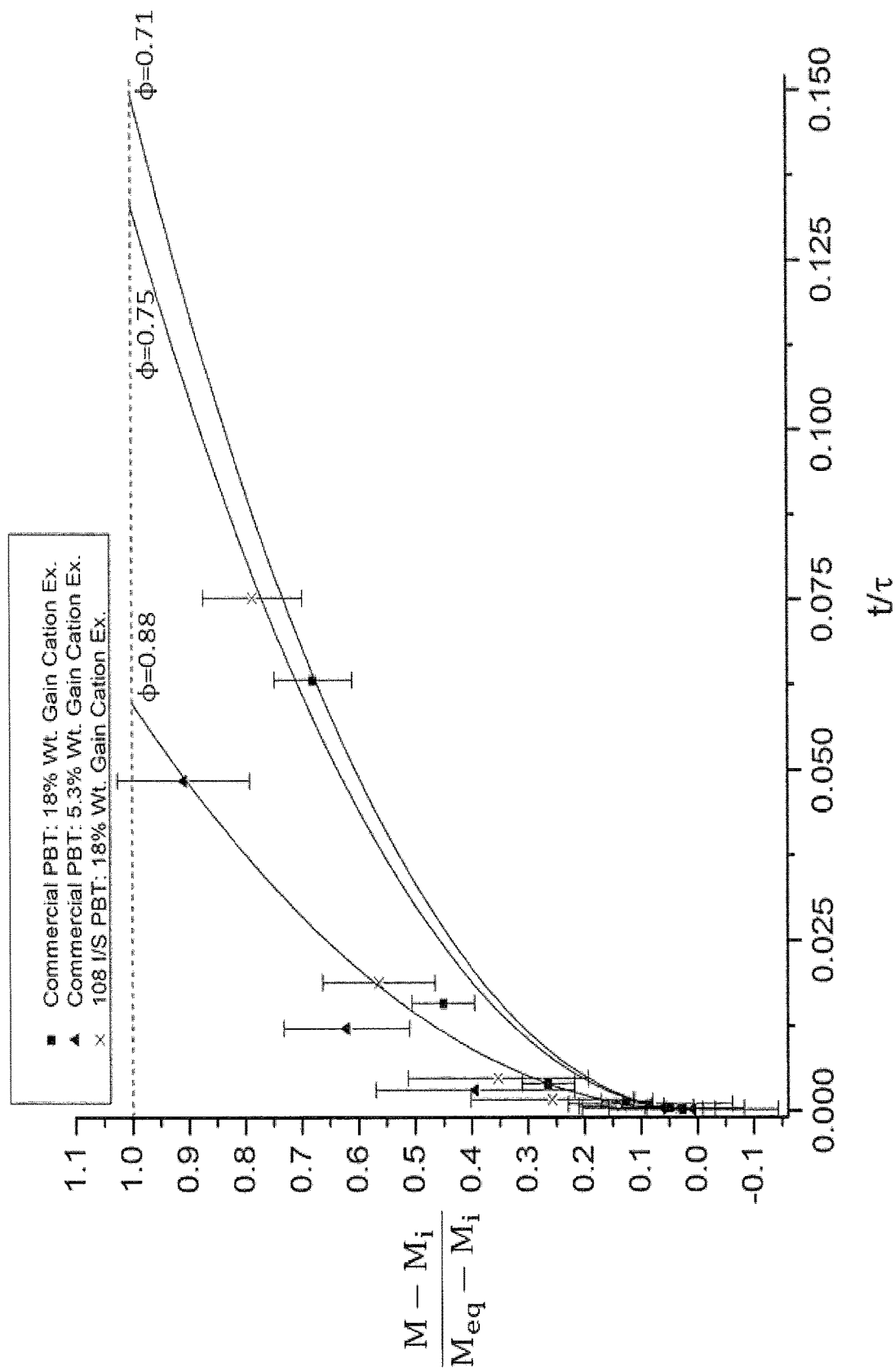
FIG. 13 is experimental and shrinking core model results for the adsorption of hIgG to cation exchange polyGMA "core" as a function of time (commercial PBT at 18% weight gain: $\phi=0.71$ and $\tau=3789$ min, commercial PBT at 5.3% weight gain: $\phi=0.88$ and $\tau=4955$ min, and 108 I/S PBT at 18% weight gain: $\phi=0.74$ and $\tau=3189$ min).

FIGS. 11 A and B show the lines of best fit for the results of $\Psi$ vs. protein contact time (t) for all the nonwovens tested in the kinetic binding experiments. The horizontal dotted and dashed lines found in FIG. 13 are the maximum values of $\Psi$ ($\Psi_{max}$) for equilibrium adsorption of the functionalized polyGMA "core" with protein for the various values of obtained in Table 3. The times at which the lines of best fit found in FIG. 13 reach $\Psi_{max}$ are the times required to reach equilibrium protein binding ($t_{eq}$). Additionally, the slopes of the lines of best fit found in FIG. 13 are equivalent to the inverse of $\tau$ as defined by Eq. 5.1. Once $\tau$ is known, values for the effective diffusivity ($D_e$) of protein transport through the "shell" can be calculated using Eq. 5.2. The values of $t_{eq}$, $\tau$, and $D_e$ are presented in Table 4.

TABLE 4

Characteristic time of adsorption ($\tau$), the time required to achieve complete conversion of the polyGMA "core" ($t_{eq}$), and the calculated effective diffusivity ($D_e$) for protein diffusion through the "shell" in the shrinking core model.

| Sample | $\tau$ (min) | $t_{eq}$ (min) | $D_e \times 10^{-13}$ (cm²/s) |
|---|---|---|---|
| Commercial PBT: 20% Wt. Gain Anion Ex. | 6716 | 876 | 7.25 |
| Commercial PBT: 5.9% Wt. Gain Anion Ex. | 3109 | 241 | 4.61 |
| 108 I/S PBT: 20% Wt. Gain Anion Ex. | 1839 | 223 | 2.47 |
| Commercial PBT: 18% Wt. Gain Cation Ex. | 3798 | 556 | 11.6 |
| Commercial PBT: 5.3% Wt. Gain Cation Ex. | 4955 | 283 | 2.61 |
| 108 I/S PBT: 18% Wt. Gain Cation Ex. | 3189 | 402 | 1.28 |

The experimental effective diffusivities obtained from the best fit values of $\tau$ for the anion exchange and cation exchange systems are shown in Table 4. For BSA diffusion through the protein filled anion exchange functionalized polyGMA layers, effective diffusivities were between $2.47 \times 10^{-13}$ and $7.25 \times 10^{-13}$ cm²/s with an average effective diffusivity of $4.77 \times 10^{-13}$ cm²/s. For hIgG diffusion through the protein filled cation exchange functionalized polyGMA layers, effective diffusivities were between $1.28 \times 10^{-13}$ and $11.6 \times 10^{-13}$ cm²/s with an average effective diffusivity of $5.16 \times 10^{-13}$ cm²/s. According to the Stokes-Einstein equation BSA and IgG have diffusion coefficients of $6.23 \times 10^{-7}$ cm²/s and $3.41 \times 10^{-7}$ cm²/s respectively, in water at room temperature. Typical pore diffusion coefficients for proteins in chromatography resins are on the order of $10^{-9}$ to $10^{-12}$

TABLE 3

Radius of swollen polyGMA layer grafted to PBT, the swollen polyGMA thickness, the effective "core" density, and $\Phi$ values for various grafted nonwoven samples.

| Sample | $r_2$ (nm) | $\delta_{swollen\ polyGMA}$ (nm) | $\rho_{core}$ (g/cm³) | $\phi = \frac{r_1}{r_2}$ |
|---|---|---|---|---|
| Commercial PBT: 20% Wt. Gain Anion Ex. | 2004.0 | 504.0 | 0.331 | 0.748 |
| Commercial PBT: 5.9% Wt. Gain Anion Ex. | 1780.6 | 280.6 | 0.187 | 0.842 |
| 108 I/S PBT: 20% Wt. Gain Anion Ex. | 610.9 | 152.9 | 0.333 | 0.750 |
| Commercial PBT: 18% Wt. Gain Cation Ex. | 2099.4 | 599.4 | 0.244 | 0.714 |
| Commercial PBT: 5.3% Wt. Gain Cation Ex. | 1699.3 | 199.3 | 0.243 | 0.883 |
| 108 I/S PBT: 18% Wt. Gain Cation Ex. | 615.0 | 157.0 | 0.291 | 0.745 |

Using the $\phi$ values presented in Table 3, the experimental data for total mass adsorbed into the membrane as a function of time can be used to fit the only remaining parameter $\tau$ in Eq. 9. From these values of $\tau$ it is then possible to estimate cm²/s. The effective diffusivities for protein capture on the ion exchange functionalized polyGMA grafted nonwovens are significantly lower than most pore diffusion coefficients in chromatography resins. It is clear that protein capture by the ion exchange functionalized polyGMA brushes suffer from a severe diffusion limitation in the polyGMA/protein "shell" depicted in FIG. 10, requiring several minutes if not hours to reach equilibrium as shown in Table 4.

The shrinking core model relies on and r to predict how protein adsorbs in the polyGMA "core" over time. Using the values for and r found in Table 3 and 4 respectively the shrinking core model results can be compared to the experimental data for protein adsorption to the functionalized polyGMA "core" as a function of time. The results for the mass adsorption of BSA to the anion exchange polyGMA "core" vs. t/τ using values of $\phi$ are shown in in FIG. 12.

Figure 12:
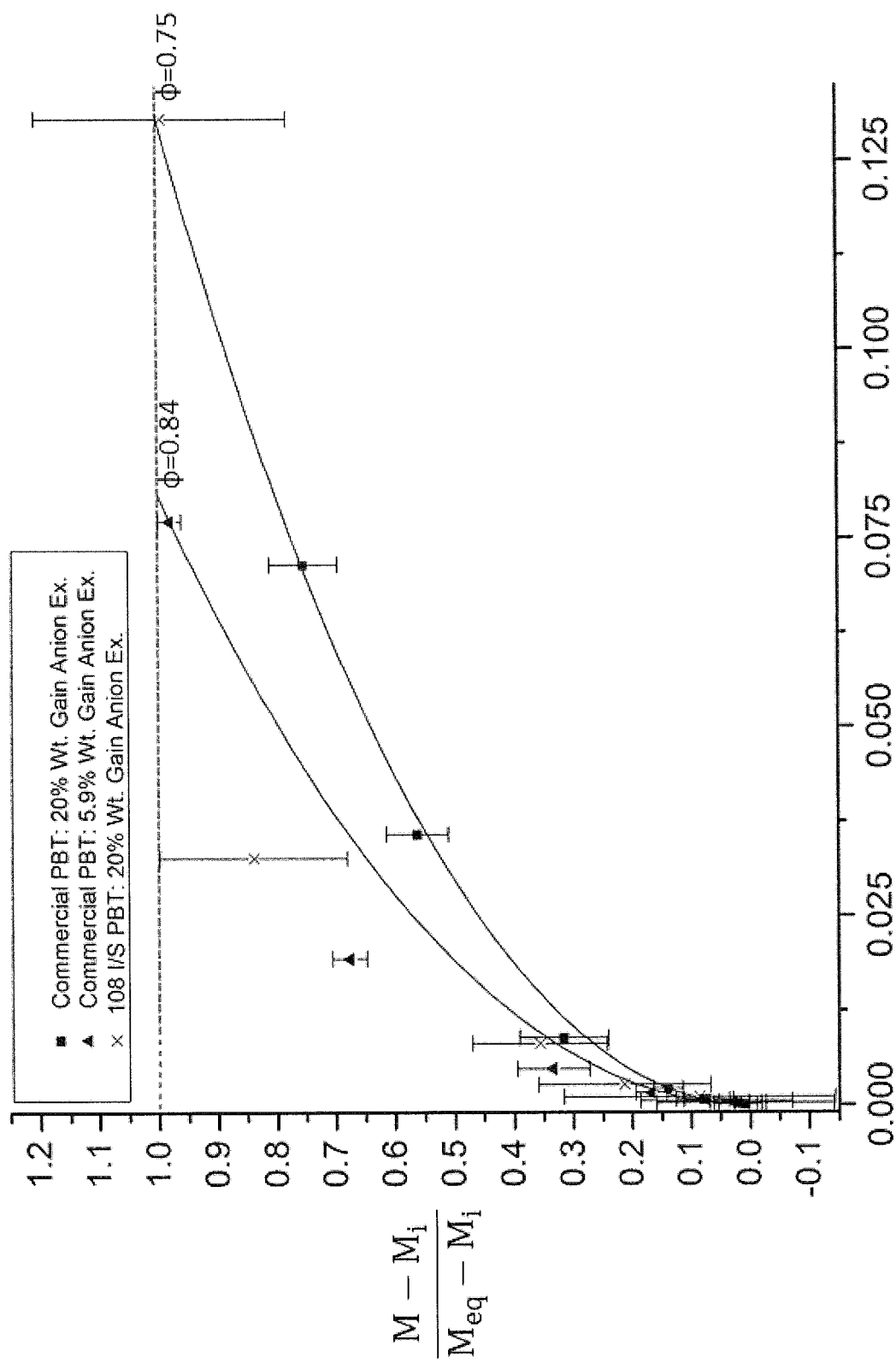
FIG. 12 is experimental and shrinking core model results for the adsorption of BSA to the anion exchange polyGMA as a function of time (commercial PBT at 20% weight gain: $\phi=0.75$ and $\tau=6716$ min, commercial PBT at 5.9% weight gain: $\phi=0.84$ and $\tau=3109$ min, and 108 I/S PBT at 20% weight gain: $\phi=0.75$ and $\tau=1839$ m)

As FIG. 12 shows, the shrinking core model provides a good approximation of the experimental data. In the shrinking core model as the thickness of the polyGMA graft increases around a given PBT fiber diameter, values of $\phi$ decrease, values for $\Psi_{max}$ increase as can be seen in FIG. 11, and the characteristic time scale of adsorption (τ) increases. Due to these reasons longer times are required to reach equilibrium for samples with thicker graft layers as can be seen in Table 4. This phenomenon can particularly be seen when comparing the commercial PBT grafted at 20% weight gain and 5.9% having swollen polyGMA brush thicknesses of 504 nm and 281 nm respectively. Both samples utilized the same starting material with different degrees of polyGMA coverage resulting in substantially different values of $\phi$, $\Psi_{max}$, and τ. Therefore, according to the shrinking core model the commercial PBT with the thinner grafted layer will exhibit a faster rate of conversion and achieve equilibrium sooner. This is observed with the commercial PBT grafted at 5.9% weight gain achieving equilibrium in 241 min compared to the commercial PBT grafted at 20% weight gain reaching equilibrium in 876 min.

The 108 I/S PBT nonwoven has a smaller PBT fiber diameter than the commercial PBT nonwoven and results in thinner grafted polyGMA brush layer as FIG. 5 displays. However, there was proportionality between the values of $r_1$ and $r_2$ for commercial PBT and the 108 I/S PBT nonwovens grafted to 20% weight gain resulting in similar values for $\phi$ and similar trends in the shrinking core model. Although the values of $\phi$ are the same for both the 108 I/S PBT nonwovens and the commercial PBT nonwovens grafted to 20% weight gain their characteristic time scales of adsorption are substantially different with τ being 1839 min for the 108 I/S nonwovens grafted at 20% weight gain and 6716 min for the commercial PBT nonwovens grafted at 20% weight gain. The smaller characteristic time scale of adsorption observed for the 108 I/S PBT nonwoven grafted at 20% weight gain results in equilibrium being reached after 223 min compared to the commercial PBT nonwovens grafted to 20% weight gain requiring 876 min to reach equilibrium. Both the commercial PBT grafted to 5.9% weight gain and the 108 I/S PBT grafted to 20% weight gain had shorter polyGMA brush thicknesses and substantially shorter times required to reach equilibrium binding, between 220 and 250 min, according to the shrinking core model compared to the commercial PBT nonwovens grafted at 20% weight gain that required almost 900 min. This is strong evidence that reducing the thickness of the polyGMA grafted layer results in faster rates of conversion of the polyGMA core and shorter times to reach equilibrium in this diffusion limited adsorption process.

The results for the conversion of the cation exchange polyGMA "core" by hIgG binding plotted vs. t/τ with the shrinking core model fit to various values of $\phi$ are presented in FIG. 13.

As FIG. 13 shows, the shrinking core model is a fair approximation of the experimental data for the different $\phi$ values. Similarly to the anion exchange nonwovens, shorter times to reach equilibrium are observed for thinner polyGMA layers for a given PBT fiber diameter. The commercial PBT grafted to 5.3% weight gain was able to achieve equilibrium in 283 min compared to polyGMA grafting of 18% weight gain that required 556 min to reach equilibrium. The 108 I/S PBT nonwoven grafted at 18% weight gain also achieved equilibrium binding in a shorter amount of time compared to the commercial PBT grafted at 18% weight gain. However, the differences in equilibrium binding time were not as large as for the anion exchange samples as Table 4 demonstrates.

The shrinking core models depicted in FIGS. 12 and 13 demonstrate a very fast initial rate of protein binding that can be seen at the very short time scales of protein binding. As a significant amount of protein binds, a "shell" that imposes a diffusion limitation for protein adsorption is created as depicted in FIG. 10. The protein bound polyGMA "shell" gets thicker over time and the distance of diffusion in this dense layer gets larger requiring longer times for protein diffusion to reach the available core for binding. This is observed in FIGS. 12 and 13 as a decreasing rate of protein adsorption both experimentally and in the shrinking core model as the material approaches equilibrium.

It is clear that protein capture by the ion exchange functionalized polyGMA brushes suffers from a severe diffusion limitation, requiring several minutes if not hours to reach equilibrium. Therefore, it is advantageous to use thinner polyGMA brush layers reducing the distance of diffusion and decreasing the required time for complete conversion. Further by using a high surface area nonwoven such as the 108 US PBT the polyGMA binding volume can be distributed in thinner layers as FIG. 5 shows, reducing capture times while still maintaining high protein binding capacities.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for preparing a polymer-grafted and functionalized nonwoven membrane adapted for use in bioseparation processes, comprising:
   i) receiving a nonwoven web comprising a plurality of islands-in-the-sea fibers or a plurality of island fibers remaining after removal of the sea component of bicomponent islands-in-the-sea fibers;
   ii) optionally, removing the sea component of the bicomponent islands-in-the-sea fibers to expose the island fibers thereof;
   iii) grafting a methacrylate polymer onto a surface of the island fibers to form a plurality of polymer segments covalently attached thereto, thereby forming grafted island fibers, the grafting step comprising contacting the nonwoven web with a solution comprising an initiator and at least one methacrylate monomer and exposing the nonwoven web to ultraviolet light having a wavelength of 365 nm and intensities between 1 and 30 mW/cm$^2$ to initiate polymerization of the at least one methacrylate monomer, wherein the nonwoven web is not subjected to a separate UV pretreatment; and iv) optionally, functionalizing the grafted island fibers to attach at least one functional group adapted for binding to a target molecule to each of the plurality of polymer segments of the grafted island fibers.

2. The method of claim 1, wherein the island fibers are constructed of polybutylene terephthalate and the methacrylate polymer is polyGMA.

3. The method of claim 1, wherein a concentration of monomer in the solution is about 5 to about 50% v/v and the initiator is present in a molar ratio of initiator to monomer of about 1:100 to about 1:5.

4. The method of claim 1, wherein the initiator is benzophenone.

5. The method of claim 1, wherein the plurality of island fibers has an average fiber diameter of less than 1.5 microns.

6. The method of claim 1, wherein the methacrylate polymer comprises one or more monomers selected from the group consisting of glycidyl methacrylate, methacrylic acid, 2-(diethylamino)ethyl methacrylate, [2-(methacryloyloxy)ethyl]trim ethyl-ammonium chloride, 2-hydroxyethyl methacrylate, 2-acrylamido-2-methylpropane sulfonic acid, 2-(dimethylamino)ethyl methacrylate, butyl methacrylate, 3-chloro-2-hydroxypropyl methacrylate, 2-ethylhexyl methacrylate, and combinations thereof.

7. The method of claim 5, wherein the average fiber diameter is about 1 micron or less.

8. The method of claim 1, wherein the at least one functional group is adapted for cation or anion exchange with the target molecule.

9. The method of claim 1, wherein the nonwoven web has a specific BET surface area of at least 1.5 $m^2/g$.

10. The method of claim 1, wherein the target molecule is a protein.

* * * * *